US012616527B2

(12) United States Patent
Kemper et al.

(10) Patent No.: US 12,616,527 B2
(45) Date of Patent: May 5, 2026

(54) SURGICAL TRACKING SYSTEM FOR TRACKING AN INSTRUMENT WITH RESPECT TO A REFERENCE BODY

(71) Applicant: Stryker European Operations Limited, Carrigtwohill (IE)

(72) Inventors: Jakob Kemper, Heemstede (NL); Lars Metz, Kiel (DE); Ulrich Hoffmann, Breisach (DE); Fabian Huegle, March (DE); Sabrina Horstmann, Kiel (DE); Peter Sterrantino, Jacksonville, FL (US)

(73) Assignee: Stryker European Operations Limited, Carrigtwohill (IE)

( * ) Notice: Subject to any disclaimer, the term of this patent is extended or adjusted under 35 U.S.C. 154(b) by 48 days.

(21) Appl. No.: 18/568,141

(22) PCT Filed: Jun. 8, 2021

(86) PCT No.: PCT/IB2021/055020
§ 371 (c)(1),
(2) Date: Dec. 7, 2023

(87) PCT Pub. No.: WO2022/259018
PCT Pub. Date: Dec. 15, 2022

(65) Prior Publication Data
US 2024/0366310 A1     Nov. 7, 2024

(51) Int. Cl.
*A61B 34/20*     (2016.01)
*A61B 34/10*     (2016.01)

(52) U.S. Cl.
CPC ........ *A61B 34/20* (2016.02); *A61B 2034/107* (2016.02); *A61B 2034/2055* (2016.02); *A61B 2034/2065* (2016.02)

(58) Field of Classification Search
CPC .......................... A61B 2034/107; A61B 34/20
See application file for complete search history.

(56) References Cited

U.S. PATENT DOCUMENTS

| | | | |
|---|---|---|---|
| 2004/0019263 A1* | 1/2004 | Jutras ..................... | A61B 90/39 600/407 |
| 2008/0208041 A1 | 8/2008 | Gilboa | |
| 2013/0211244 A1* | 8/2013 | Nathaniel .............. | A61B 34/20 600/424 |
| 2014/0107471 A1 | 4/2014 | Haider et al. | |

(Continued)

FOREIGN PATENT DOCUMENTS

| | | |
|---|---|---|
| EP | 2 436 333 A1 | 4/2012 |
| EP | 2 769 689 A1 | 8/2014 |

(Continued)

OTHER PUBLICATIONS

International Search Report for PCT/IB2021/055020 mailed Feb. 3, 2022. 5 pgs.

(Continued)

*Primary Examiner* — John D Li

(74) *Attorney, Agent, or Firm* — Lerner David LLP

(57) ABSTRACT

Surgical guiding device, a surgical reference body (50) and a surgical tracking system (2), and in particular to a surgical guiding device, a surgical reference body and a surgical tracking system allowing an improved localization of surgical components.

19 Claims, 9 Drawing Sheets

(56) References Cited

U.S. PATENT DOCUMENTS

| 2014/0243658 A1 | | 8/2014 | Breisacher et al. | |
| 2015/0150641 A1 | * | 6/2015 | Daon ..................... | A61B 34/20 |
| | | | | 600/424 |
| 2015/0265370 A1 | | 9/2015 | Garbey et al. | |
| 2018/0049622 A1 | | 2/2018 | Ryan et al. | |
| 2018/0318035 A1 | * | 11/2018 | Mclachlin .............. | A61B 90/94 |
| 2019/0192125 A1 | * | 6/2019 | Coakley ............. | A61B 10/0241 |
| 2020/0330180 A1 | | 10/2020 | Olive et al. | |
| 2020/0375436 A1 | * | 12/2020 | Kielack .................. | A61B 90/50 |
| 2021/0030486 A1 | * | 2/2021 | Zhang ................... | A61B 34/20 |

FOREIGN PATENT DOCUMENTS

| JP | 2019534717 A | 12/2019 | | |
| WO | 2015/022100 A1 | 2/2015 | | |
| WO | WO-2020194302 A1 | * | 10/2020 | ............... A61N 7/02 |

OTHER PUBLICATIONS

Communication pursuant to Article 94(3) EPC for European Application No. 21732560.4 dated Feb. 17, 2026. 11 pgs.

* cited by examiner

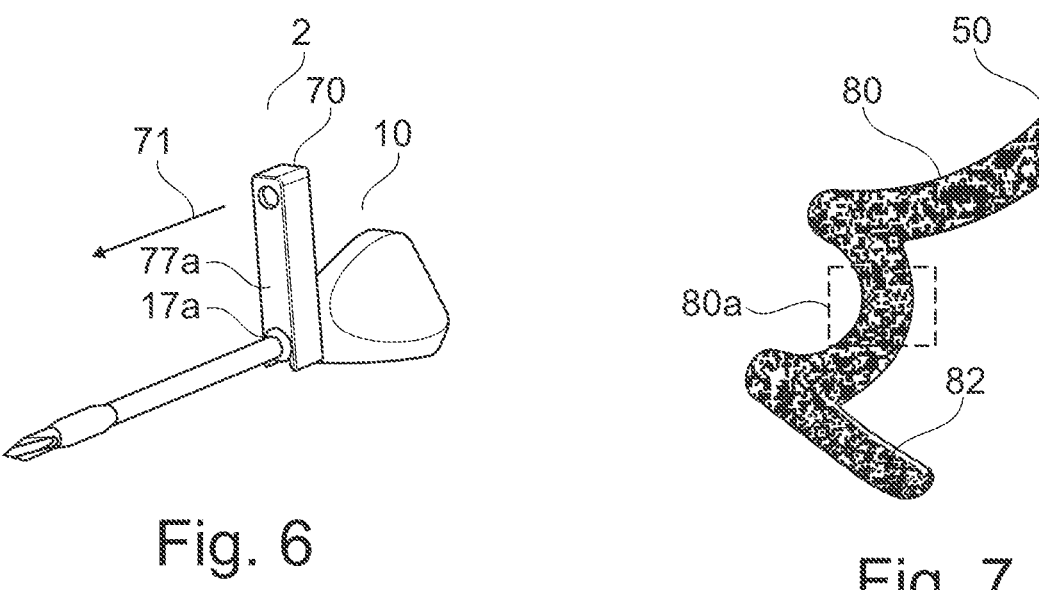
Fig. 6
Fig. 7
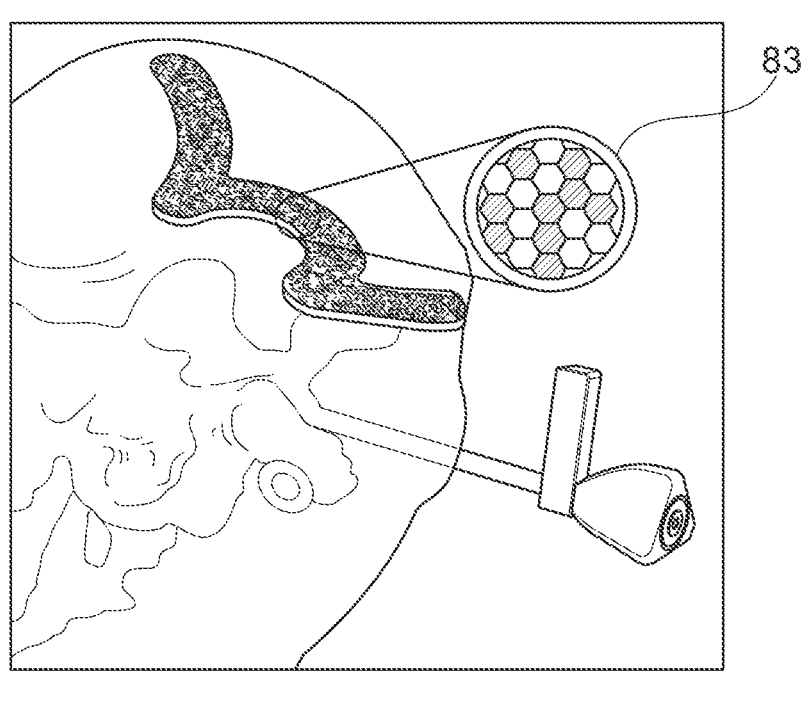
Fig. 8

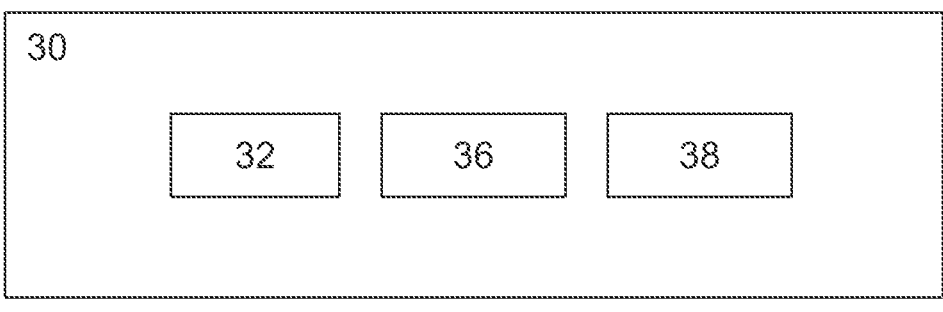
Fig. 9
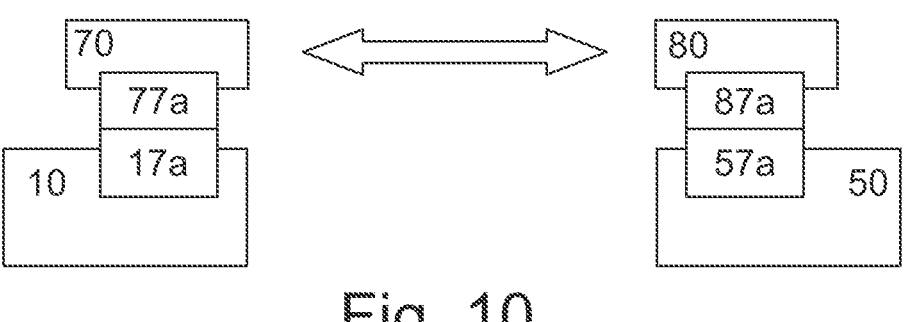
Fig. 10
Fig. 11

$$60 = 61 + 62 (+63)$$
$$65 = 66 + 67 (+68)$$

SURGICAL TRACKING SYSTEM FOR TRACKING AN INSTRUMENT WITH RESPECT TO A REFERENCE BODY

CROSS-REFERENCE TO RELATED APPLICATIONS

The present application is a national phase entry under 35 U.S.C. § 371 of International Application No. PCT/IB2021/055020, filed Jun. 8, 2021, published in English, the disclosures of which are incorporated herein by reference.

FIELD OF THE INVENTION

The present invention relates to a surgical guiding device, a surgical reference body and a surgical tracking system, and in particular to a surgical guiding device, a surgical reference body and a surgical tracking system allowing an improved localization of surgical components, and a corresponding method, computer program product and storage medium having stored thereon the computer program product.

BACKGROUND OF THE INVENTION

Surgical procedures have improved over the recent years. Significant improvements have been achieved by supporting systems for supporting the clinical personal in particular surgeons during surgeries. In particular bone fractures benefit from supporting systems for surgeons, which provide the surgeon with equipment, which allows the surgeon to improve exactness of repositioning of bone parts and positioning of implants, like screws, nails and bone plates, as well as tools and targeting and guiding devices.

As traumatized bones, i.e. fractures, have only a limited visual access, monitoring is usually based on radiating principles, like X-ray imaging or computer tomography CT images, or magnet resonance tomography MRT images. All these principles and methods involve at least one of the drawbacks of being radiation intensive, requiring large devices and requiring a considerable amount of time. Each monitoring step during a surgery prolongs the surgery duration and thus the duration of narcotic impact and increases costs and radiation impact.

Therefore, there is a need for surgical guiding devices, surgical reference bodies and surgical tracking systems as well as corresponding methods, which reduce imaging effort and thus duration of the surgery, reduce radiation impact on the patient, but at the same time maintain or increase the level of exactness of the surgery.

SUMMARY OF THE INVENTION

The present invention provides a surgical guiding device, a surgical reference body and a surgical tracking system, allowing an improved localization and positioning of surgical components, and corresponding methods, computer program products and storage mediums having stored therein the computer program product(s) according the subject matter of the independent claims. Further embodiments are incorporated into the dependent claims.

According to an embodiment of the invention there is provided a surgical tracking system for tracking a surgical instrument with respect to a surgical reference body, the surgical tracking system comprises an optical imaging device representing a position and orientation of one of a surgical instrument and a surgical reference body, the optical imaging device having a predetermined viewing direction;

an optical pattern representing a position and orientation of the other of said surgical instrument and said surgical reference body, the optical pattern having at least one unique optical sub-pattern, which allows determination of a relative position and orientation of said surgical reference body with respect to the position and orientation of said surgical instrument; an image processing device comprising pattern recognition means being adapted for recognizing the position and orientation of the at least sub-pattern of the optical pattern with respect to a position and viewing direction of the imaging device based on an image taken from the optical imaging device and a stored representation of the optical pattern, and visualization means being adapted for virtually visualizing a surgical instrument represented by the respective one of the optical imaging device and the optical pattern and virtually visualizing a surgical reference body represented by the respective other of the optical pattern and the optical imaging device.

Thus, the relative position of an optical imaging device and an optical pattern can be determined. If the optical pattern is known with respect to its structure and size, an image thereof allows to determine from where the image was taken. It is not required to take an image of the entire pattern, as long as the imaged portion of the pattern is unique in the entire pattern. Both, the optical imaging device and the optical pattern represent either a surgical instrument or a surgical reference body. It should be noted that the optical imaging device and the optical pattern may also represent other items for which it is required to determine their relative position with respect to each other. It is also possible that the entire surgical tracking system supports more than one optical imaging device and it also possible to support more than one optical pattern. The optical pattern may be printed onto a surgical instrument or a reference body. If printed onto, embedded in or fixed to an item, the pattern makes the item to a reference body, as the pattern allows an optical referencing. If embedded or fixed to an item, the optical imaging device makes the item to a reference body as it allows optical referencing. For optical determination of a relative position and orientation, it is required that the relative position and relative imaging or viewing direction of the optical imaging device with respect to the item is knows which is represented by the optical imaging device. Likewise, it is required that the optical pattern as such is known, as well as its relative position and relative orientation with respect to the item is known, which is represented by the optical pattern. If the relative position and orientation of the optical imaging device and the optical pattern with respect to each other can be determined, and the relative position and orientation of the each of the optical imaging device and the optical pattern with respect to the respective item is known which is represented by them, then it is possible to determine the relative position and orientation of the items with respect to each other and to visualize the position and orientation of the items with respect to each other, which may be a visualization of a surgical tool and a reference body being attached to a patient's anatomy.

According to an embodiment of the invention there is provided a surgical tracking system for tracking a first part of a surgical reference body with respect to a second part of a surgical reference body, the surgical tracking system comprises an optical imaging device representing a position and orientation of one of a first part of a surgical reference body and a second part of a surgical reference body, the optical imaging device having a predetermined viewing direction; an optical pattern representing a position and orientation of the other of said first part of a surgical reference body and said second part of a surgical reference body, the optical pattern having at least one unique optical sub-pattern, which allows determination of a relative position and orientation of said first part of a surgical reference body with respect to the position and orientation of said second part of a surgical instrument; an image processing device comprising pattern recognition means being adapted for recognizing the position and orientation of the at least sub-pattern of the optical pattern with respect to a position and viewing direction of the imaging device based on an image taken from the optical imaging device and a stored representation of the optical pattern, and computation means being adapted for determination of a relative position and orientation of said first part of a surgical reference body with respect to the position and orientation of said second part of a surgical instrument.

Thus, the relative position of an optical imaging device and an optical pattern can be determined. If the optical pattern is known with respect to its structure and size, an image thereof allows to determine from where the image was taken. It is not required to take an image of the entire pattern, as long as the imaged portion of the pattern is unique in the entire pattern. Both, the optical imaging device and the optical pattern represent either a first part of a surgical reference body or second part of a surgical reference body. It is also possible that the entire surgical tracking system supports more than one optical imaging device and it also possible to support more than one optical pattern, so as to determine the relative spatial position and orientation of more than two parts of a surgical reference body. The optical pattern may be printed onto a respective part of the surgical reference body. If printed onto, embedded in or fixed to a part of the surgical reference body, the pattern makes the part of the surgical reference body to a reference body, as the pattern allows an optical referencing. For optical determination of a relative position and orientation, it is required that the relative position and relative imaging or viewing direction of the optical imaging device with respect to the part of the surgical reference body is known which is represented by the optical imaging device. Likewise, it is required that the optical pattern as such is known, as well as its relative position and relative orientation with respect to the part of the surgical reference body is known, which is represented by the optical pattern. If the relative position and orientation of the optical imaging device and the optical pattern with respect to each other can be determined, and the relative position and orientation of the each of the optical imaging device and the optical pattern with respect to the respective part of the surgical reference body is known which is represented by them, then it is possible to determine the relative position and orientation of the parts of the surgical reference body with respect to each other. This may be applied to extractable surgical reference bodies, which have at least two parts, one of which is provided with the optical pattern and the other of which is provided with the optical imaging device. The two or more parts of the surgical reference body may be used to be adapted to patient's anatomies which are very large and cannot be imaged by a single radio image. The parts, each of which may have a radio dense geometry or sub-geometry each having a unique projection in a radio image, may be illustrated in separate radio images. The spatial position and orientation can be carried out with the optical imaging device coupled to one part of the reference body and an optical pattern coupled to the other part of the surgical reference body, so that with the optical determination of the relative spatial position, also the spatial position of the radio dense (sub) geometries can be determined, including the bone parts of e.g. long bones, which are referenced with the parts of the surgical reference body. The parts of the surgical reference body may coupled to each other by a mechanical structure which selectively allows fixing and releasing of the parts of the surgical reference body with respect to each other. This can be done via a rail or a hinge, each having only one degree of freedom, or by a combination of one or more rail and one or more hinges allowing more than one degree of freedom. It should be noted that what is described in the following for a surgical instrument and a reference body also applies for a first part of a surgical reference body and a second part of a surgical reference body.

According to an embodiment the surgical tracking system further comprises augmenting means being adapted for augmenting a predetermined operating trajectory of a surgical instrument onto the virtual visualization of the surgical instrument, based on a recognized position and orientation of the at least sub-pattern of the optical pattern with respect to a position and viewing direction of the imaging device, so as to visualize an operating path of the surgical instrument relative to a surgical reference body represented by the optical pattern.

Thus, not only the items represented by the optical imaging device and the optical pattern can be visualized, but additional information can be augmented. An operating path of a surgical instrument may be a trajectory along which an implant or tool may travel when guided by the surgical instrument, be it within the surgical instrument or outside or in extension of the surgical instrument, or an operating range and radius of a tool connected to the surgical instrument, or a contour of an implant to be implanted, which may be guided by the surgical instrument. Augmentation may also include augmenting a variety of items, e.g. different sizes of an implant, which are applies by the surgical tool. Augmenting varieties may take place at the same time or interleaved.

According to an embodiment augmenting means may include a scroll means which can be used by a surgeon to selectively scroll through a variety of different items, like different tools, implant sizes or implant types until he has identified the best matching implant.

Thus, it is possible to easily find the right tool, by scrolling through e.g. different drill diameters, different implant sizes, different implant types or varieties, in particular implants which have sub-implants. If for example a bone nail is augmented, different varieties of nails including its locking screw varieties can be augmented, so that the surgeon not only recognizes the main implant, but may also decide whether a main implant is suitable, if e.g. the augmented locking screw thereof collides with an anatomy, which is not suitable for receiving a locking screw. Scrolling through the varieties may allow selection of the right implant like a nail and sub-implant like a locking screw can be selected within seconds.

According to an embodiment, the optical imaging device comprises a mechanical interface to be coupled to a positive fit receptacle of one of a surgical instrument and a surgical reference body for forming a unit having a reproducible relation between a geometry of said one of a surgical instrument and a surgical reference body, and the position and viewing direction of the optical imaging device.

Thus, it can be guaranteed that the relative position and orientation of the optical imaging device with respect to the connected surgical instrument and reference body, respectively, is established. The positive fit receptacle can also have a key and keyhole coded portion, which allows connections only for particular combinations, for which the relative position and orientation is known to the system. This may avoid unintended misuse and misinterpretations during operation. The mechanical interface allows to release the unit for selectively re-using of the components.

According to an embodiment the surgical tracking system further comprises a surgical instrument, wherein the surgical instrument comprises a mechanical interface for the mechanical interface of the optical imaging device so as to form a reproducible relation between the geometry of the surgical instrument and the position and viewing direction of the optical imaging device.

Thus, not only the optical imaging device is provided, but also the surgical instrument, to which the optical instrument is releasable coupled via the interface.

According to an embodiment the surgical tracking system further comprises a surgical reference body, wherein the surgical reference body comprises a mechanical interface for the mechanical interface of the optical imaging device so as to form a reproducible relation between the geometry of the surgical reference body and the position and viewing direction of the optical imaging device.

Thus, not only the optical imaging device is provided, but also the surgical reference body, to which the optical instrument is releasable coupled. This also illustrates that the optical imaging device can be coupled not only to a surgical instrument, but also the surgical reference body.

According to an embodiment the optical pattern comprises a mechanical interface to be coupled to a positive fit mechanical interface of one of a surgical instrument and a surgical reference body for forming a unit having a reproducible relation between a geometry of said one of a surgical instrument and a surgical reference body, and the position and orientation of the optical pattern.

Thus, it can be guaranteed that the relative position and orientation of the optical pattern with respect to the connected surgical instrument and reference body, respectively, is established. The positive fit receptacle can also have a key and keyhole coded portion, which allows connections only for particular combinations, for which the relative position and orientation is known to the system. This may avoid unintended misuse and misinterpretations during operation.

According to an embodiment, the surgical tracking system further comprised a surgical instrument, wherein the surgical instrument comprises a mechanical interface for the mechanical interface of the optical pattern so as to form a reproducible relation between the geometry of the surgical instrument and the position and orientation of the optical pattern.

Thus, not only the optical imaging device is provided, but also the surgical instrument, to which the optical pattern is releasable coupled via the interface.

According to an embodiment the surgical tracking system further comprises a surgical reference body, wherein the surgical reference body comprises a mechanical interface for the mechanical interface of the optical pattern so as to form a reproducible relation between the geometry of the surgical reference body and the position and orientation of the optical pattern.

Thus, not only the optical pattern is provided, but also the surgical reference body, to which the optical pattern is releasable coupled. This also illustrates that the optical pattern can be coupled not only to a surgical instrument, but also the surgical reference body.

According to an embodiment the surgical tracking system further comprises a surgical instrument, wherein the optical imaging device is inseparably connected to the surgical instrument so as to form a reproducible relation between the geometry of the surgical instrument and the position and orientation of the optical imaging device.

Thus, it is possible to establish a reliable allocation of the optical imaging device and the surgical instrument, without running into the risk to connect the optical imaging device to a surgical instrument, which is not intended for that use.

According to an embodiment the surgical tracking system further comprises a surgical reference body, wherein the optical pattern is inseparably connected to the surgical reference body so as to form a reproducible relation between the geometry of the surgical reference body and the position and orientation of the optical pattern.

Thus, it is possible to establish a reliable allocation of the optical pattern and the surgical reference body, without running into the risk to connect the optical pattern to a surgical reference body, which is not intended for that use.

According to an embodiment the surgical tracking system further comprises a surgical instrument, wherein the optical pattern is inseparably connected to the surgical instrument so as to form a reproducible relation between the geometry of the surgical instrument and the position and orientation of the optical pattern.

Thus, it is possible to establish a reliable allocation of the optical pattern and the surgical instrument, without running into the risk to connect the optical pattern to a surgical instrument, which is not intended for that use.

According to an embodiment the surgical tracking system further comprises a surgical reference body, wherein the optical imaging device is inseparably connected to the surgical reference body so as to form a reproducible relation between the geometry of the surgical reference body and the position and orientation of the optical imaging device.

Thus, it is possible to establish a reliable allocation of the optical imaging device and the surgical reference body, without running into the risk to connect the optical imaging device to a surgical reference body, which is not intended for that use.

According to an embodiment the optical pattern is composed of a geometrically even raster of light and dark fields, in particular a raster of squared light and dark fields, in particular a raster of light and black fields.

Thus, it is easier to reproduce the orientation and position of the pattern. Further, the printing process is easier to realize and the pattern can be easier calculated. The fields of different colors or shades in the squared raster form a unique pattern area. Geometrically even means that the dimensions of the fields is geometrically even, but each field the can have different colors or shades for forming the unique pattern area.

According to an embodiment the optical pattern is composed of a geometrically even raster of fields of different colors, in particular a raster of squared colored fields, in particular a raster of color gradient fields.

Thus, not only light and dark fields can be used, but also different colors. This allows a color coding which makes it easier for a surgeon to select the right optical pattern. Further when using instead of two options more than two colors, i.e. light and dark, then more information can be stored on the same surface portion. With two options, e.g. light and dark, two fields can reflect four different combinations. With four options, e.g. yellow, blue, red, green, two fields can reflect sixteen different combinations, which is four times more.

According to an embodiment the optical pattern is composed of a honeycomb raster of light and dark fields, in particular a raster of light and dark circles or hexagons in a honeycomb raster, in particular a raster of light and black circles or hexagons.

Thus, a more compact pattern may be provided, as each field of a honeycomb raster is closer to a circle compared to a squared raster. The packing density is higher than with a squared pattern. The fields of different colors or shades in the honeycomb raster form a unique pattern area.

According to an embodiment the optical pattern is composed of a honeycomb raster fields of different colors, in particular a raster of colored circles or hexagons in a honeycomb raster, in particular a raster of color gradient circles or hexagons.

Thus, not only light and dark fields can be used, but also different colors. This allows a color coding which makes it easier for a surgeon to select the right optical pattern. Further when using instead of two options more than two colors, i.e. light and dark, then more information can be stored on the same surface portion. With two options, e.g. light and dark, two fields can reflect four different combinations. With four options, e.g. yellow, blue, red, green, two fields can reflect sixteen different combinations, which is four times more.

According to an embodiment the surgical instrument is a surgical guiding device and further comprises a guiding body having a longitudinal extension from a proximal end of the surgical guiding device to a distal end of the surgical guiding device, and being adapted for guiding at least one of a longitudinal surgical implant and a longitudinal tool, and having a guiding trajectory extending along the guiding body and succeeding in distal direction along a traveling path of at least one of a surgical implant and a surgical tool to be inserted and guided; and a radio dense geometry being located in a predetermined spatial position and orientation with respect to the guiding body, and being adapted for providing a unique radio projection for each proximal to distal orientation of the guiding body.

According to an embodiment the surgical reference body comprises a radio dense geometry being fixedly and spatially reproducibly connected to the surgical reference body, a reference body portion having an anatomically adapted surface for a patient's anatomy, wherein the radio dense geometry has a unique radio projection for each proximal to distal orientation of the surgical reference body, so that the radio dense geometry allows determination of the spatial position and orientation of the surgical reference body based on a two dimensional radio projection of at least a part of the surgical reference body.

Thus, it is possible to not only determine the relative position and orientation based on an optical pattern recognition and identification, but at the same time monitoring the surgical reference body, be it in form of an integrally formed reference body or an attachable reference body, also by radio monitoring. Thus, both identification options can be provided, which also may be used at the same time.

According to an embodiment the surgical reference body comprises a radio dense geometry having a first radio dense sub-geometry and a second radio dense sub-geometry each being fixedly and spatially reproducibly connected to the surgical reference body; a first reference body portion having an anatomically adapted surface for a patient's anatomy; and a second reference body portion having an anatomically adapted surface for a patient's anatomy, wherein each of the first radio dense sub-geometry and the second radio dense sub-geometry has a unique radio projection for each proximal to distal orientation of the surgical reference body, so that each of the first radio dense sub-geometry and the second radio dense sub-geometry alone allows determination of the spatial position and orientation of the surgical reference body based on a two dimensional radio projection of at least a part of the surgical reference body, wherein the first radio dense sub-geometry is allocated to the first reference body portion, and the second radio dense sub-geometry is allocated to the second reference body portion.

Thus, it is possible reduce the focus on the relevant portion of the reference body, in particular when using a larger reference body. The construction of the legs allows covering a large surface of the patient's anatomy, but allows access between the legs. Such reference body may be used with pelvis surgeries, where the pelvis region requires a reliable referencing by a reference body, which covers large regions of the pelvis. Depending on the viewing direction upon radio imaging, only parts of the entire reference body may be seen in a radio image. Therefore, it is relevant that position and orientation can be determined even if having only a partial view. If providing a plurality of radio dense sub-geometry, each allowing the determination of the spatial position and orientation, it is very likely that at least one of the radio dense sub-geometries is within the imaged portion, and thus allows determination of the position and orientation of the reference body.

According to an embodiment the surgical reference body comprises a radio dense geometry having a first radio dense sub-geometry, a second radio dense sub-geometry, and a third radio dense sub-geometry each being fixedly and spatially reproducibly connected to the surgical reference body; a first leg having an anatomically adapted surface for a patient's anatomy; and a second leg having an anatomically adapted surface for a patient's anatomy, wherein the first leg with a first end is connected to a first end of the second leg at a leg joining portion, wherein each of the first radio dense sub-geometry, the second radio dense sub-geometry, and the third radio dense sub-geometry has a unique radio projection for each proximal to distal orientation of the surgical reference body, so that each of the first radio dense sub-geometry, the second radio dense sub-geometry, and the third radio dense sub-geometry alone allows determination of the spatial position and orientation of the surgical reference body based on a two dimensional radio projection of at least a part of the surgical reference body, wherein the first radio dense sub-geometry is allocated to a second end of the first leg, the second radio dense sub-geometry is allocated to a second end of the second leg, and the third radio dense sub-geometry is allocated to the leg joining portion of the first leg and the second leg.

Thus, with the three radio dense sub-geometries a more distributed arrangement of radio dense sub-geometries can be achieved. This increases a probability that within each taken radio image a projection of a radio dense sub-geometry can be found, which allows determination of the spatial position and orientation of the imaged part.

According to an embodiment the surgical reference body comprises at least one apex-pin hole.

Thus, it is possible to fix the surgical reference body to a patient's anatomy, so that the spatial position and orientation between the reference body and the patient's anatomy can be established and maintained. It should be noted that it is also possible to provide more than one apex hole. It should be noted that beside one or more apex-pin holes also one or more interfaces may be provided for coupling the optical imaging device or the optical pattern. Such interfaces usually are provided at the surface side facing away from the surface side being used for being adhered to the patient's anatomy.

According to an embodiment the at least one apex-pin hole is located between the first end and the second end of at least one of the first leg and the second leg.

Thus, the apex-pin hole can be provided at a certain distance to the radio dense sub-geometries, if these radio dense sub-geometries are located at the end portions of the leg and at the joining portion of the legs. It should be noted that instead of using an apex pin hole, the reference body may also fixed to patients anatomy via e.g. loops for Velcro attachment, connecting elements for pins or to an additional surgical instrument e.g. with a railway to clamp Hoffmann system.

According to an embodiment at least one of the first leg and the second leg comprises a first sub-leg and a second sub-leg, wherein a first end of the first sub-leg corresponds to the first end of the at least one of the first leg and the second leg, and the second end of the first sub-leg corresponds to the first end of the second sub-leg at a sub-leg joining portion.

Thus, the first and second sub-leg allow an arrangement where the leg trajectory follows a patient's anatomy.

According to an embodiment the sub-leg joining portion comprises at least one of the at least one apex-pin holes.

Thus, the apex hole can be provided at the joining portion of the first and second sub-leg. The joining portion of the first and second sub-leg may correspond to an expose bone of the patient, where the bone is close to the skin, so that an apex-pin can be mounted to the bone of the patient's anatomy.

According to an embodiment an angle between the first leg and the second leg at its joining point is less than 90°, particularly less than 60°.

Thus, a compact framework of legs can be provided. The trajectory of the legs may be bent, the bending may be in a form so as to open the angle.

According to an embodiment an angle between the first sub-leg and the second sub-leg at its joining point is less than 90°, particularly less than 60°.

Thus, a compact framework of legs can be provided. The trajectory of the legs may be bent, the bending may be in a form so as to open the angle.

According to an embodiment the first sub-leg and second sub-leg of one of the first leg and second leg, and the other of the first leg and second leg forms a W-shape.

Thus, the entire reference body may be adapted to the patient's anatomy, in particular the pelvis region of the patient's anatomy. The W-shape allows a stable framework of legs and sub-legs, provides sufficient open space between the legs at the relevant parts of the patient's anatomy and allows a sufficient adoption to the patient's pelvis anatomy, in particular where patient's bones are exposed to be close to the skin surface, which allows a reliable fixing and positional and orientation referencing between the reference body and the patient's anatomy.

According to an embodiment at least a part of the anatomically adapted surfaces comprises an adhering means.

Thus, the reference device may be easily adhered to the patient's anatomy, without additional injury. However, the adhering may also take place in addition to the application to the apex-pin.

According to an embodiment the adhering means comprises a portion, which is a surface portion coated with an adhesive, which is not irritant to human skin.

Thus, the reference body may be easily fixed to the patient's anatomy. The adhesive may be activated or deactivated by applying a particular temperature or radiation.

According to an embodiment the adhering means comprises a portion, which is one part of a touch fastener, a counterpart thereof is adhereable to human skin.

Thus, the reference body may be easily fixed to the patient's anatomy and upon misalignment, the position of the reference body may be corrected easily.

According to an embodiment of the invention, there is provided a method for visualizing tracking of a surgical instrument with respect to a surgical reference body, the method comprises taking an optical image toward a predetermined viewing direction by an imaging device mounted with a predetermined viewing direction onto one of a surgical instrument and a surgical reference body, of an optical pattern mounted with a predetermined relative position and orientation to the other of said surgical instrument and said surgical reference body, wherein the optical pattern having at least one unique optical sub-pattern, which allows determination of a relative position and orientation of said surgical reference body with respect to the position and orientation of said surgical instrument, processing a taken optical image of the optical pattern by recognizing the at least one sub-pattern of the optical pattern, comparing the recognized optical sub-pattern with a stored representation of the optical pattern, and determining from a size, an orientation and a distortion of the recognized sub-pattern compared to the stored representation of the optical pattern the position and orientation of the surgical instrument with respect to orientation and position of the surgical reference body.

According to an embodiment the method further comprises visualizing a surgical instrument represented by one of the optical imaging device and the optical pattern and visualizing a surgical reference body represented by the other of the optical imaging device and the optical pattern.

According to an embodiment the method further comprises augmenting a predetermined operating trajectory of the surgical instrument onto a virtual visualization of the surgical instrument, based on a recognized position and orientation of the at least sub-pattern of the optical pattern with respect to a position and viewing direction of the imaging device, so as to visualize an operating path of the surgical instrument relative to a surgical reference body represented by the optical pattern.

According to an embodiment of the invention, there is provided a computer program product, which when carried out executes the method as describe above.

According to an embodiment of the invention, there is provided a data storage medium having stored thereon an executable code of the computer program product as described above.

It should be noted that the above described embodiments may also be combined and in a combined form provide a synergetic technical effect and synergetic benefits which go beyond the sum of the single technical effects and benefits.

BRIEF DESCRIPTION OF THE FIGURES

The invention will be described by way of the following drawings, which illustrate in FIG. 1: illustrates an exemplary embodiment of a surgical guiding device/surgical instrument/tool in a lateral view.

FIG. 6: illustrates an exemplary embodiment of a surgical guiding device/surgical instrument/tool having mounted thereon an optical imaging device.

FIG. 7: illustrates an exemplary embodiment of a surgical reference body having a squared optical pattern.

FIG. 8: illustrates an exemplary embodiment of a surgical reference body having a hexagonal optical pattern applied to a patient's anatomy, together with a surgical guiding device/ surgical instrument/tool having mounted thereon an optical imaging device.

FIG. 9: illustrates a schematic view of an exemplary embodiment of an image processing device.

FIG. 10: illustrates an exemplary embodiment where the optical imaging device is connected to the surgical tool via respective interfaces and the pattern is connected to the reference body connected via respective interfaces.

FIG. 11: illustrates an exemplary embodiment where the optical imaging device is connected to the reference body via respective interfaces and the pattern is connected to the surgical tool connected via respective interfaces.

It should be noted that same or similar reference numerals illustrate same or similar components. Along these Figures exemplary embodiments of the invention will be describes as follows.

DETAILED DESCRIPTION OF EXEMPLARY EMBODIMENTS

Figures 1, 2:
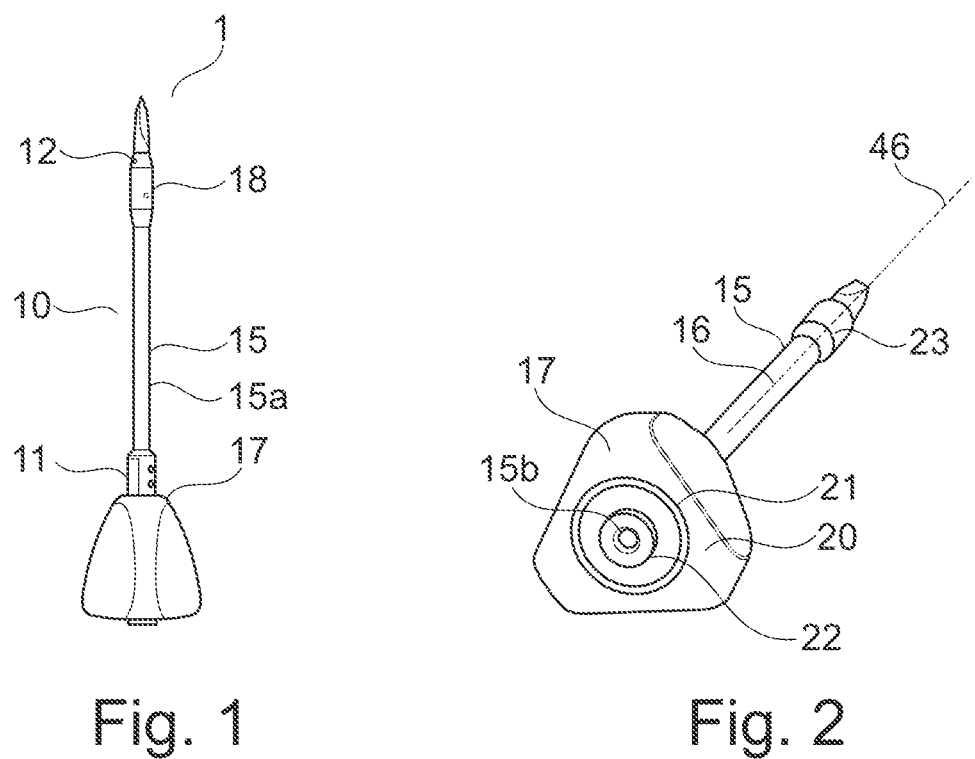
FIG. 2: illustrates an exemplary embodiment of a surgical guiding device/surgical instrument/tool in a perspective view seen from proximal to distal direction.

For a surgical implant and a surgical tool, the distal end is defined as the end firstly entered into a patient's body, and the proximal end is defined as the opposite end. For a drilling tool, the end including the drilling geometry is considered as being the distal end and the shaft for fixing the drilling tool to a drilling drive is considered as being the proximal end.

A (radio) projection is considered as projected image of a geometry onto a two-dimensional array.

Complementary patterns of a first and second radio dense sub-geometry are considered as matching patterns, which together form a closed common pattern. Such matching patterns may be formed e.g. by concentric circles or polygons or other shapes having a uniform circumferential distance or overlap, by interleaving segments having a uniform distance or overlap like segments of a circle or polygons or other shapes, etc.

Centre line of a tool, an implant or a part thereof is the imaginary line, which follows a path, which has an equal distance to the lateral edges of the respective tool, implant or part thereof.

Joining point of two legs is considered as the point where the both centerlines of the two legs cross each other or have the smallest distance.

Angle between two legs is considered as an angle defined by a tangent of the centerlines of the respective legs running through a joining point of the both centerlines.

Joining portion of two legs is the area where the both legs toward their joining point are no longer separated, i.e. commonly share their edges.

Complementary patterns of a first and second radio dense sub-geometry are considered as matching patterns, which together form a closed common pattern. Such matching patterns may be formed e.g. by concentric circles or polygons or other shapes having a uniform circumferential distance or overlap, by interleaving segments having a uniform distance or overlap like segments of a circle or polygons or other shapes, etc.

Virtually visualizing a surgical guiding device or a surgical instrument may include a full visualization of the surgical guiding device and surgical instrument, respectively, but in addition or alternatively may also include visualization of a characteristic geometry, which may be an axis of the surgical guiding device and surgical instrument, respectively, and/or a representative scale and/or contour thereof. Virtually visualizing a surgical guiding device or a surgical instrument may also include a visualization of an available variety of implants or the like, e.g. visualizing three different available bone screws, in particular in combination with the patient's anatomy to which a screw is intended to be applied, so that the surgeon may recognize and identify through the virtually visualization the suitable screw out of the variety of screws. It should be noted that this is not limited to the number of three and also not limited to screws, but may also include nails, in particular nails with varying curve radius and other implants and surgical instruments like k-wires and the like.

A unique projection of any intended use orientation of the surgical guiding device or a surgical instrument, does not exclude that a projection of two or more different orientations are identical, as long as the system and/or the surgeon recognizes that the second and each further orientation with identical projection are outside an intended or reasonable use. With this respect a repeated pattern projection may be acceptable, if it always guaranteed, that the orientation within an intended or reasonable use range can be determined based on the unique projection. Outside an intended or reasonable use may be seen if the surgical guiding device or a surgical instrument is upside down oriented or toward an orientation, which cannot lead to serious injuries during surgery.

The correspondence between a reference body and a patient's anatomy can be established by providing a plurality (two or more) images from different positions/orientations (e.g. ML, AP or any other different directions) with the reference body being attached to the patient's anatomy. Based on these plurality of views the relation between the reference body and the patient's anatomy is achieved by image augmentation. The known geometry of a reference body allows determining the scaling of the reference body and the instrument/tool/anatomy in the imaging plane. The different imaging views may be referenced with respect to each other. Further, an automated or manual 2D-image segmentation can be carried out for setting different reference bodies in relation to a patient's anatomy. This can be supported by a database, which includes generally known bone geometries or individually known bone geometries, which can be obtained by e.g. a postoperative CT or the like.

FIG. 1 and FIG. 2 illustrate a surgical guiding system 1 for computer-assisted-surgery CAS. The surgical guiding system 1 comprises a surgical guiding device 10, which is here illustrated as an awl. The surgical guiding device 10 comprises a guiding body 15 having a longitudinal extension from a proximal end 11 of the surgical guiding device to a distal end 12 of the surgical guiding device 10. The guiding body has a hollow shaft 15a, and being adapted for guiding at least one of a longitudinal surgical implant and a longitudinal tool. The surgical implant may be e.g. a screw or a nail or a wire. A tool may be a k-wire, a drill or a needle. The hollow shaft 15a has a guiding channel 15b, wherein the guiding channel follows the guiding trajectory 16 extending along the guiding body and succeeding in distal direction along a traveling path 46 of a surgical implant or a surgical tool to be inserted and guided.

The guiding trajectory may be straight or may be bent or curved. A straight trajectory may be used for inserting straight implants or tolls, like a drill or a screw. A bent trajectory may be used for inserting bent or curved implants or tools, like bent nails, or bent wires. The guiding trajectory is to be understood as the trajectory within or on the guiding body 15 or hollow shaft. The traveling path 46 is to be understood as a path extending the guiding path 16 toward the distal direction, i.e. the direction pointing toward the patient. The traveling path usually has a similar curvature as the guiding trajectory 16. If the guiding trajectory 16 is straight, also the traveling path 46 is straight. If the guiding path is curved, usually also the traveling path along which a curved implant or tool is traveling is curved. The traveling path defines the path the guided implant or tool when being inserted travels after exiting the hollow shaft 15a at the distal end, which is here illustrated as the tip 18 of the tool. The here illustrated awl has a handle or knob 17, which is used for handling the awl, in particular for applying a blade at the distal end 12 of the awl. The blade may leave an opening through which a tool or implant may be guided through the hollow shaft and through the distal opening toward the patient.

It should be understood that although FIGS. 1 and 2 illustrate an awl, the guiding device 10 may also be a targeting device for positioning a nail or a screw.

FIG. 2 illustrates at the knob 17 a radio dense geometry 20. The radio dense geometry 20 is located in a predetermined spatial position and orientation with respect to the guiding body 15. The radio dense geometry 20 provides a unique radio projection 25 for any proximal to distal orientation of the guiding body in an intended use orientation of the surgical guiding device 10. As the unique projection allows determining the orientation of the guiding device 10 and thus the guiding body 15 and the hollow shaft 15a, the unique projection can be used for determining the guiding trajectory 16 and the traveling path 46 along which a tool or implant travels when being guided by the hollow shaft 15a. It should be noted that the hollow shaft may also have a lateral slit (not illustrated here) for laterally inserting an implant or tool. This slit may be closed by a cover so as to for a closed hollow shaft 15a. The guiding body (15) comprises a hollow shaft (15a) with a guiding channel (15b), wherein the guiding channel follows the guiding trajectory (16).

The radio dense geometry 20 may have a first radio dense sub-geometry 21 and a second radio dense sub-geometry 22. The first and second radio dense sub-geometries 21, 22 in this illustration are located at the knob 17, but may also be located somewhere on the guiding device 10. Any radio dense geometry 20 or sub-geometry 21, 22, 23 may also be provided as a releasable mounted geometry, e.g. with a clip connection. Sub-geometry 21, 22 may be formed together in a clip. Matching key-keyhole elements on the guiding device and the radio dense geometry 20 or a radio dense sub-geometry 21/22, 23 may establish a predefined orientation and position of the radio dense geometry 20/sub-geometry 21, 22, 23 with respect to the guiding device. The key/keyhole components may also be used that only radio dense geometries 20/sub-geometries 21, 22, 23 which are intended for being used with the guiding device 10 can be clipped to the guiding device. The radio dense geometry may have a unique three-dimensional shape and/or may be composed of sub-geometries together forming the unique projection.

Figure 5:
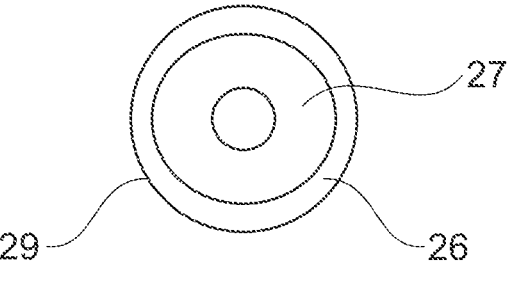
FIG. 5: illustrates a complimentary match of a first and second radio dense sub-geometry.

The first radio dense sub-geometry 21 and the second radio dense sub-geometry 22 may be realized by two circular rings of a radio opaque material, as illustrated in FIG. 2, which are concentrically arranged but not in the same plane but parallel planed. If having a view straight from the proximal to the distal direction, both rings in the projection appear as concentric circles. In this viewing direction the both rings, one of the first radio dense sub-geometry 21 and one of the second radio dense sub-geometry 22 may form a complimentary pattern, here two concentric rings, which may fit into each other. If applying an inclined view from slightly lateral positon, the rings appear as ellipses and no longer concentric. The measure of the concentric shift and the measure of the elliptic deformation, as well as the relative size of the both rings may give a basis for calculating not only the lateral viewing angle, but also the viewing distance. As the geometry of the guiding device is known, also its guiding trajectory 16 is knows and thus the traveling path 46. This applies not only for a straight guiding trajectory, but also to a curved guiding trajectory 16. The radio projection 26 of the first radio dense sub-geometry 21 and the radio projection 27 of the second radio dense sub-geometry 22 together in a predetermined viewing direction, which may be toward the straight longitudinal extension, may have a complementary pattern 29, as illustrated in FIG. 5. This complementary pattern 29 may be formed by e.g. the both concentric rings. Other complementary patterns may be formed by any key/keyhole shapes matching to each other when viewing toward the complementary viewing direction.

Figure 4:
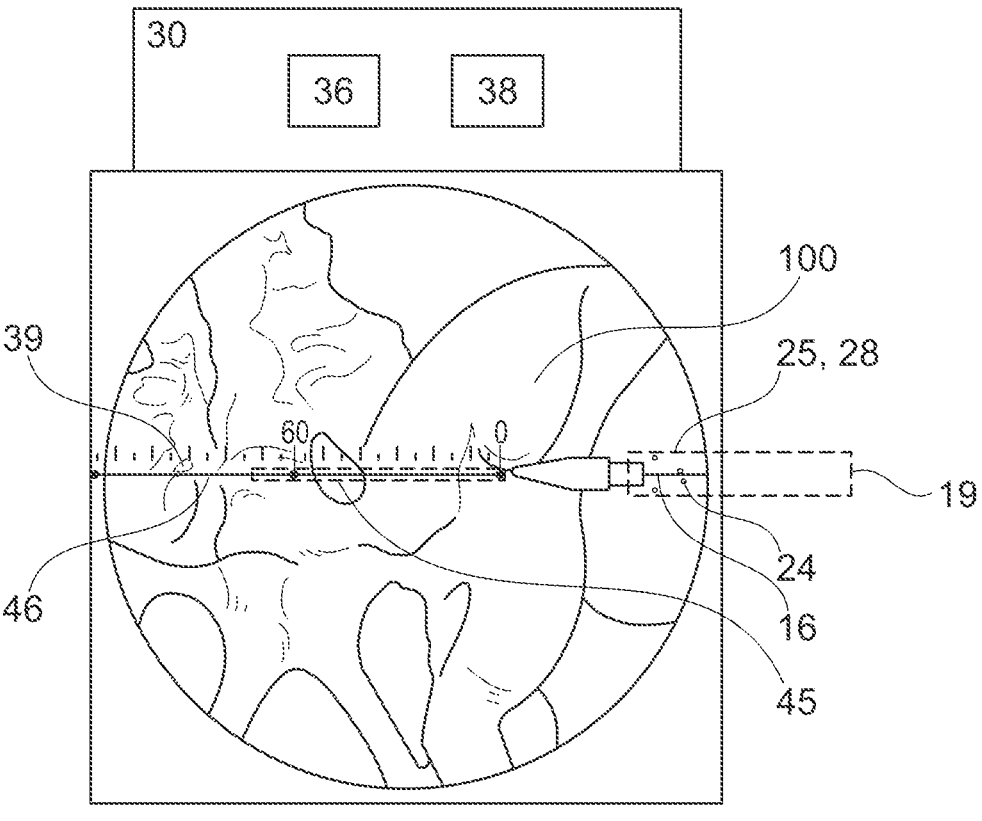
FIG. 4: illustrates a side view in a radio image of a surgical guiding device/surgical instrument/tool applied to a patient's anatomy.

As illustrated in FIG. 2 the guiding device may have a further, a third radio dense sub-geometry 23. Whereas the first and second radio dense sub-geometries 21 and 22 in the shown embodiment are located at the proximal end 11 with the knob 17, the third radio dense sub-geometry 23 is located close to the distal end 12 and the tip 18. The third radio dense sub-geometry 23 may be provided with fiducial markers 24, as illustrated in FIG. 4. It should be noted that the third radio dense sub-geometry 23 may also be provided at the proximal end 11 and may also spatially overlap with the first and second radio dense sub-geometries 21 and 22. Fiducial markers 24 may be radio opaque spheres or other geometries, which are spatially arranged so as to commonly provide unique projection for any viewing direction. The concentric circles of the first and second radio dense sub-geometries 21 and 22 may allow a very exact determination of the exact proximal to distal direction, the fiducial markers 24 may allow an exact lateral determination of the spatial orientation.

Figure 3:
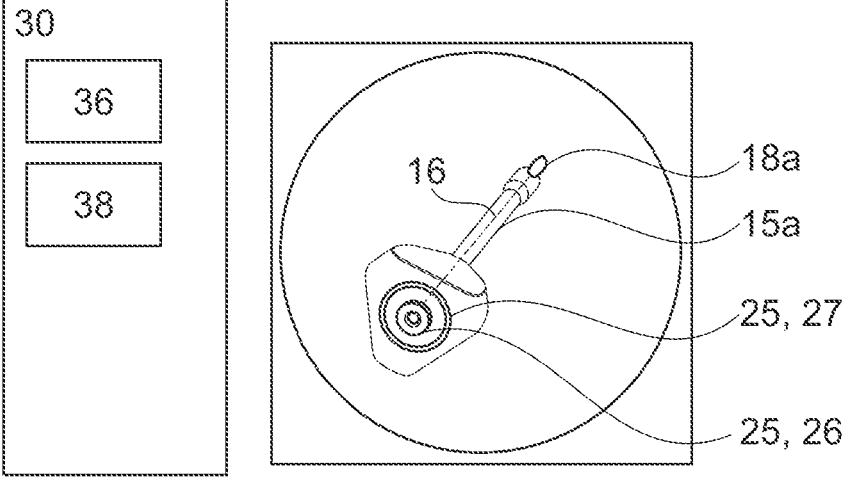
FIG. 3: illustrates an exemplary embodiment of a surgical guiding device/surgical instrument/tool in a perspective view seen from proximal to distal direction in a radio image.

FIG. 3 illustrates the visualization of the first radio dense sub-geometry 21 with its unique radio projection 26. The radio dense geometry 20, 21, 22, 23 allows a more exact determination as the contour of the guiding device, in particular if the contour of the guiding device is of no high contrast. Based on the position, size and shape of the both rings of the first radio dense sub-geometry 21, it is possible to determine the orientation of the guiding device 10, and to augment and visualize the guiding trajectory 16, as well as the traveling path 46.

The visualization and augmentation can be conducted by an image processing device 30, which may be a computer or any other computational capacity. The image processing device has a visualization means 36 being adapted for a virtual visualization 19 of the orientation of the guiding body 15 with respect to a patient's anatomy 100, based on the unique radio projection 25 of the radio dense geometry 20, here of the third radio dense sub-geometry 23 with its fiducial markers 24, as illustrated in FIG. 4. The unique radio projection 27 of the third radio dense sub-geometry 23, in particular the pattern of the fiducial markers 24, allows a determination of the position and orientation of the guiding device. This allows a virtual visualization 19 of the orientation of the guiding body 15. The image processing device 30 further has an augmenting means 38 for augmenting the guiding trajectory 16 onto the virtual visualization 19 of the orientation of the guiding body 15, so as to visualize a traveling path 46 of at least one of a surgical implant or a surgical tool 45 to be implanted.

In order to simplify the orientation of the surgeon, the augmenting means 38 may augment a reproducible scale 39 along the augmented guiding trajectory 16. This scale 39 may give the surgeon an idea where an implant tip or tool tip will end when being inserted along the guiding trajectory 16. This scale may also support the surgeon in selecting the correct implant/tool length. In combination with an image recognition and anatomy identification, a suggestion may be made t the surgeon which tool or implant is recommended to be used. The augmenting means may also augment a geometry related to an implant to be implanted with respect to a patient's anatomy 100, based on the unique radio projection 25 of the radio dense geometry 20, in particular based on the unique radio projection 27 of the fiducial markers 24 of the third radio dense sub-geometry 23, as illustrated in FIG. 4.

FIGS. 6 and 7 illustrate a surgical tracking system for tracking a surgical instrument 10 with respect to a surgical reference body 50. The surgical tracking system 2 has an optical imaging device 70 and an optical pattern 80. The imaging device 70 takes an image of the pattern 80, and as the pattern has unique portions, the size, distortion and recognized unique pattern portion allows determination of the relative position of the optical imaging device 70 and the pattern 80. The imaging device 70 may be camera or any other image taking device. The imaging device may be coupled to either a surgical tool 10 or a reference body 50 to be attached to a patient's anatomy. The pattern 80 may be coupled to the other of the reference body 50 and the optical imaging device 70. FIG. 5 illustrates that the optical imaging device 70 is coupled to the surgical tool/device 10. FIG. 6 illustrates that the optical pattern 80 is coupled to the reference body 50. Here the pattern 80 is printed directly to the reference body 50. It should be noted that the pattern can also be provided on the surgical instrument/tool 10 side and the optical imaging device 70 may be provided at the reference body 50 side. Both, the pattern 80 and the optical imaging device 70 may be fixedly coupled to the respective instrument 10 and reference body 50, respectively, or may be releasable coupled thereto. It also possible to releasable couple the optical imaging device 70 to the surgical instrument 10, so as to re-use a valuable camera device, whereas the pattern 80 may be un-releasable printed onto the reference body 10, which may be disposed after use.

The imaging device 70, when being mounted to a surgical instrument 10, represents a position and orientation of the surgical instrument 10 with respect to a predetermined viewing direction 71 of the optical imaging device 70), and likewise the optical pattern 80 represents a position and orientation of the surgical reference body 50 with respect to the unique optical sub-pattern 80a. Thus, taking an image from the pattern 80 allows determination of a relative position and orientation of said surgical reference body 50 with respect to the position and orientation of said surgical instrument 10. For this purpose the system is provided with an image processing device 30 having a pattern recognition means 32 and a visualization means 38, as illustrated in FIG. 9. Further the image processing device 30 may have an augmenting means 36.

The image processing device 30 has a pattern recognition means 32 for recognizing the position and orientation of the at least sub-pattern 80a of the optical pattern 80 with respect to a position and viewing direction 71 of the imaging device 70 based on an image taken from the optical imaging device 70 and a stored representation of the optical pattern. Further, the image processing device 30 has a visualization means 38 for virtually visualizing a surgical instrument 10 represented by the optical imaging device 70 and virtually visualizing a surgical reference body 50 represented by the optical pattern 80. Alternatively, the visualization means 38 virtually visualize a surgical instrument 10 represented by the optical pattern 80 and virtually visualize a surgical reference body 50 represented by the optical imaging device 70, depending onto which of the instrument 10 and the reference body 50, the imaging device 70 and the pattern 80 are mounted. If an augmenting means 36 is provided, the augmenting means may augment a moving axis or trajectory of an instrument, a scale or even a virtual instrument or a virtual implant to the visualization. The augmented items may be provided from a conversion process which converts at least two 2-dimensional images to a 3-dimansional image, or from virtually stores items from a data basis. Further, additional information may be augmented, like quantitative scales, implant properties or identifiers etc., which may help the surgeon in identifying the correct measures and items. The augmenting means may augment a predetermined operating trajectory 16, 46 of a surgical instrument 10 onto the virtual visualization of the surgical instrument 10, based on a recognized position and orientation of the at least sub-pattern 80a of the optical pattern 80 with respect to a position and viewing direction 71 of the imaging device 70, so as to visualize an operating path 46 of the surgical instrument 10 relative to a surgical reference body 50 represented by the optical pattern 80. This augmenting may take place on a screen or even in augmenting glasses worn by the surgeon during surgery.

FIG. 10 and FIG. 11 illustrate that the optical imaging device 70 may have a mechanical interface 77a to be coupled to a positive fit receptacle 17a, 57a of one of the surgical instrument 10 and the surgical reference body 50 for forming a unit having a reproducible relation between a geometry of said one of a surgical instrument 10 and a surgical reference body 50, and the position and viewing direction 71 of the optical imaging device 70. Likewise, the optical pattern 80 may comprises a mechanical interface 87a to be coupled to a positive fit mechanical interface 17a, 57a of one of a surgical instrument 10 and a surgical reference body 50 for forming a unit having a reproducible relation between a geometry of said one of a surgical instrument 10 and a surgical reference body 50, and the position and orientation of the optical pattern 80. Instead of providing releasable receptacles, it is also possible to fixedly connect the optical imaging device 70 to one of the surgical instrument 10 and the surgical reference body 50 for forming a unit having a reproducible relation between a geometry of said one of a surgical instrument 10 and a surgical reference body 50, and the position and viewing direction 71 of the optical imaging device 70. Likewise, the optical pattern 80 may fixedly mounted to the other one of a surgical instrument 10 and a surgical reference body 50 for forming a unit having a reproducible relation between a geometry of said one of a surgical instrument 10 and a surgical reference body 50, and the position and orientation of the optical pattern 80.

As illustrated in FIG. 7, the optical pattern 80 is composed of a geometrically even raster 82 of light and dark fields. The fields may be squared or round fields or have a shape which has a certain fit to a rectangular raster. The color of the raster fields may be any differing color, including printing dark or black fields onto a light or white or metallic surface, e.g. an anodized surface of an implant, tool, reference body or the like. In in particular a raster of squared light and dark fields, in particular a raster of light and black field may be used similar to a QR code. Certain anchor patterns may be used for claiming defined sub-patterns. Instead of light and dark or black and white fields, also fields of different color may be used, e.g. red and green, yellow and blue or yellow and black. As an alternative, the optical pattern 80 may be composed of a honeycomb raster 83 of light and dark fields, as illustrated in FIG. 8. The fields may be hexagonal or round fields or have a shape which has a certain fit to a honeycomb raster. The color of the honeycomb raster fields may be any differing color, including printing dark or black fields onto a light or white or metallic surface, e.g. an anodized surface of an implant, tool, reference body or the like. In in particular a raster of squared light and dark fields. Instead of light and dark or black and white fields, also fields of different color may be used, e.g. red and green, yellow and blue or yellow and black.

Figure 12:
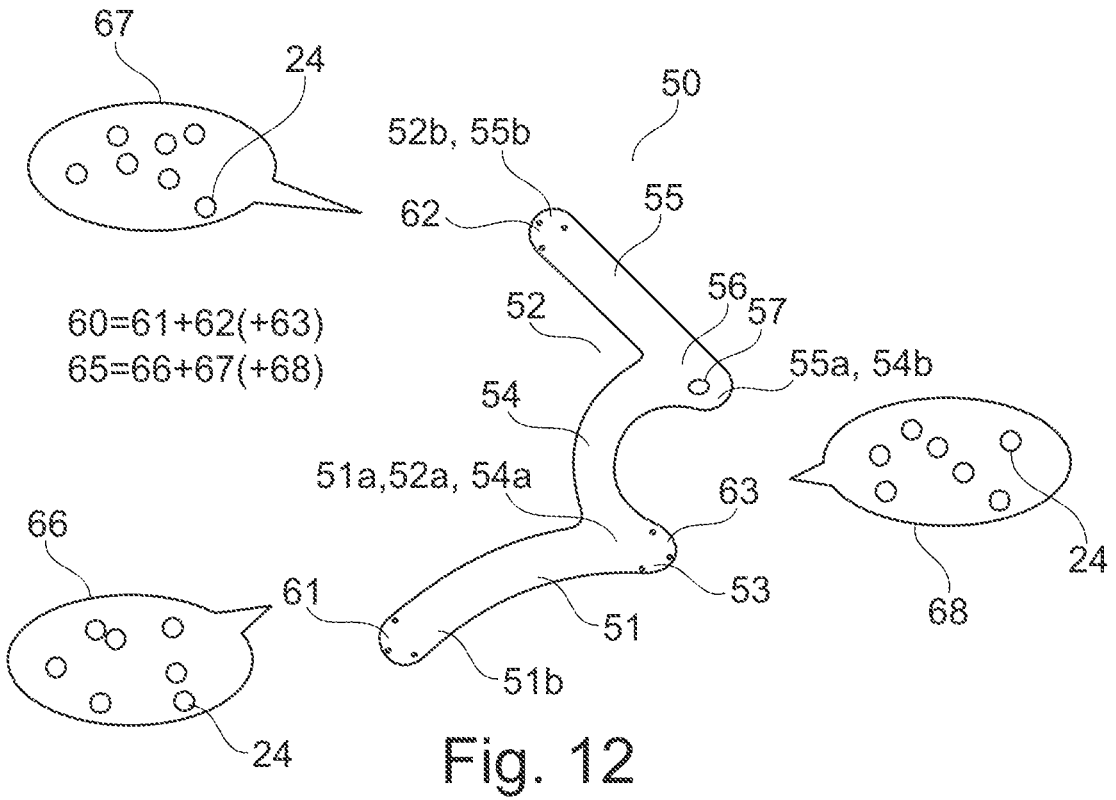
FIG. 12: illustrates an exemplary embodiment of a W-shaped surgical reference body including unique radio projections of the different radio dense sub-geometries.

FIG. 12 illustrates a shape of a surgical reference body 50, which may be aligned to a patient's anatomy 100, as it is illustrated in FIG. 8.

The surgical reference body 50 for radio based identification purposes as a radio dense geometry 60 having a first radio dense sub-geometry 61 and a second radio dense sub-geometry 62 each being fixedly and spatially reproducibly connected to the surgical reference body 50. The reference body 50 (which is not illustrated in its general form here) has a first leg 51 and a second leg 52, each having an anatomically adapted surface 59 for a patient's anatomy 100. The anatomically adapted surface is illustrated in FIG.

13. The first leg 51 with a first end 51a is connected to a first end 52a of the second leg 52 at a leg joining portion 53. Each of the first radio dense sub-geometry 61 and the second radio dense sub-geometry 62 has a unique radio projection 66, 67 for each proximal to distal orientation of the surgical reference body 50, so that each of the first radio dense sub-geometry 61 and the second radio dense sub-geometry 62 alone allows determination of the spatial position and orientation of the surgical reference body 50 based on a two dimensional radio projection of at least a part of the surgical reference body. The radio dense geometry may be formed by a set of fiducial markers 24 as described with respect to FIGS. 1 to 4, in particular FIG. 4. The radio dense geometry of the sub-geometries 61, 62 may also be provided by the pattern 80, where e.g. the dark fields of the pattern are made of radio dense material or paint. The first radio dense sub-geometry 61 is allocated to the first leg 51 and the second radio dense sub-geometry 62 is allocated to a second leg 52. In a particular embodiment, the first radio dense sub-geometry 61 is allocated to a second end 51b of the first leg 51 and the second radio dense sub-geometry 62 is allocated to a second end 52b of the second leg 52.

Figure 13:
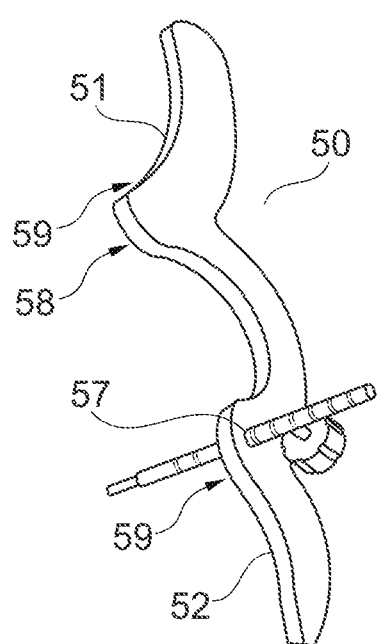
FIG. 13: illustrates an exemplary embodiment of a W-shaped surgical reference body having applied thereto an apex-pin in an apex-pin hole.

FIG. 12 illustrates a surgical reference body 50 for referencing a patient's anatomy during surgery and having a radio dense geometry 60 having a first radio dense sub-geometry 61, a second radio dense sub-geometry 62, and a third radio dense sub-geometry 63. Each of the sub-geometries is fixedly and spatially reproducibly connected to the surgical reference body 50. The radio dense sub-geometries may be provided as a set of fiducial markers, as illustrated e.g. in FIG. 4, but may also be provided as a raster as illustrated in FIG. 2 or FIG. 3, where e.g. the dark fields are made of a radio dense material and the light fields are not covered by a radio dense material. The first and second leg 51, 52 have an anatomically adapted surface 59 for a patient's anatomy 100, as illustrated in FIG. 8 and FIG. 13. The first leg 51 with a first end 51a is connected to a first end 52a of the second leg 52 at a leg joining portion 53. Each of the first radio dense sub-geometry 61, the second radio dense sub-geometry 62, and the third radio dense sub-geometry 63 has a unique radio projection 66, 67, 68 for each proximal to distal orientation of the surgical reference body 50, so that each of the first radio dense sub-geometry 61, the second radio dense sub-geometry 62, and the third radio dense sub-geometry 63 alone allows determination of the spatial position and orientation of the surgical reference body 50 based on a two dimensional radio projection of at least a part of the surgical reference body. The first radio dense sub-geometry 61 is allocated to a second end 51b of the first leg 51, the second radio dense sub-geometry 62 is allocated to a second end 52b of the second leg 52, and the third radio dense sub-geometry 63 is allocated to the leg joining portion 53 of the first leg 51 and the second leg 52.

FIG. 12 illustrates that the surgical reference body 50 comprises an apex-pin hole 57. The reference body 50 also may have further apex-holes, although not illustrated. The apex-pin hole 57 here is located between the first end 52a and the second end 52b of the second leg 52. As illustrated in FIG. 12, at least one of the first leg 51 and the second leg 52, here in FIG. 12 the second leg 52, is composed of a first sub-leg 54 and a second sub-leg 55, wherein a first end 54a of the first sub-leg 54 corresponds to the first end 52a of the second leg 52, and the second end 54b of the first sub-leg 54 corresponds to the first end 55a of the second sub-leg 55 at a sub-leg joining portion 56. In this illustrated embodiment, the sub-leg joining portion 56 comprises the apex-pin hole 57. The apex-pin hole 57 may receive an apex pin, as illustrated in FIG. 13. The illustrated reference body 50 may have a W-shape, wherein the first sub-leg 54 and second sub-leg 55 of the second leg, and the first leg 51 form the W-shape. For fixing the reference body 50 to a patient's anatomy, the reference body 50 may have on at least a part of the anatomically adapted surfaces 59 an adhering means 58. The adhering means may be a portion, which is a surface portion coated with an adhesive, which is not irritant to human skin. Alternatively or at a different surface portion the adhering means 58 comprises a portion, which is one part of a touch fastener, a counterpart thereof is adhereable to human skin.

Figure 14:
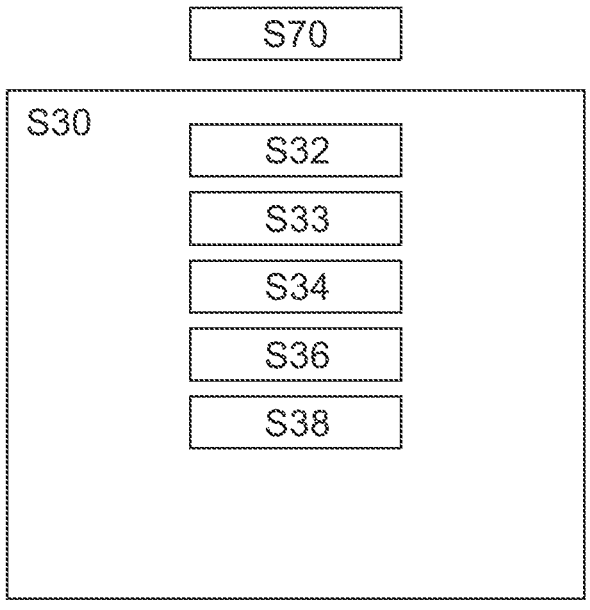
FIG. 14: illustrates an exemplary embodiment of a method with mandatory and optional method steps.

FIG. 14 illustrates a method for assisting positioning an application of implants/tools with respect to a patient's anatomy. The method includes processing imaging S30, which may include recognizing pattern(s) S32 and comparing recognized (sub-)pattern(s) with predetermined pattern(s) S33. Further, processing imaging S30 may include determining position and orientation of (sub-)pattern(s) S34, visualization S36 of the items and augmenting S38 e.g. a guiding trajectory, implant/tool/instrument contours or illustrations. For providing a relative position and orientation of an optical imaging device and an optical pattern, the method may include taking an optical image S70 of the pattern with the imaging device.

Wedge osteotomies are a common treatment for mid-foot deformities (like flatfoot or Charcot foot). The current approach is to use freehand osteotomies under fluoroscopic guidance using a C-arm. Even if proper planning based on CT-data is used, the main challenge is to execute the plan during the surgery. This often results in challenging surgeries, imprecise corrections and insufficient fixation strength. The solution described here is an extension to the above described patter recognition where a camera can determine its position in space relative to an optical pattern on another device and a technology based on stereotactic, where the relationship of radio image positions and instruments in the radio image can be calculated and augmented with additional information like trajectories, measurements and other 3D information. The aspect described in the following combines a fluoroscopic reference body 50 and a camera 70 mounted on to a targeting instrument like a cut-guide, plate inserter or a drill sleeve. The reference-body 50 is a rigid structure fixed to the patient's anatomy 100, e.g. a foot through adhesives or pins, that allows to relate all fluoroscopic images of interest to each other. The reference-body also encompasses the optical reference pattern 80, as described above. The camera 70 mounted on the targeting-device can then determine its position relative to the reference-body 50. This way, the current trajectory/plane/position of the targeting instrument 10, 15 can be indicated on all previously acquired images that have the reference-body 50 in their field of view. This allows in a first step to register the planning that was originally done on 3D CT data with the x-ray images or radio images. This also allows the display of the planned wedge onto all x-ray images or radio images taken during the surgery as a reference. In the next step this information can be used to help the surgeon to align the guiding bodies 15, 15a, 15b as cutting guides by either use an incremental approach based on the stereotactic approach with radio-opaque markers 20, 24 in the cut-guide that are visible in the x-ray/radio image so that the system can show the current position of the cut plane 16, 16a, 16b based on current tool position in the radio image relative to the planned cuts 101a, 101b. When using this approach, this information could also be given without taking additional radio images on all needed planes at once. Once the cut guides 15, 15a, 15b have been placed according the plan and cuts have been performed, the system also allows the verification of the actual repositioning compared with the initial plan. For placement of the implant like plate 45 or nail an insertion tool in combination with a camera 70 can be used that would allow live feedback on implant placement. By using the similar principle on a drill guide the screws can be placed using either a stereotactic optical image based approach giving additional information like trajectory, length, and diameter. This could be enhanced with collision warning or screw length suggestion by the system based on the underlying anatomical structure. In comparison to standard radio or fluoro-navigation, this solution requires significantly less hardware, less trackers and referencing and minimizes the field of vision issue to only one camera needing the reference-body in its field of vision, a drastic reduction of complexity while offering very comparable functionality, as will be described with respect to the following described figures.

Figures 15, 16, 17, 18:
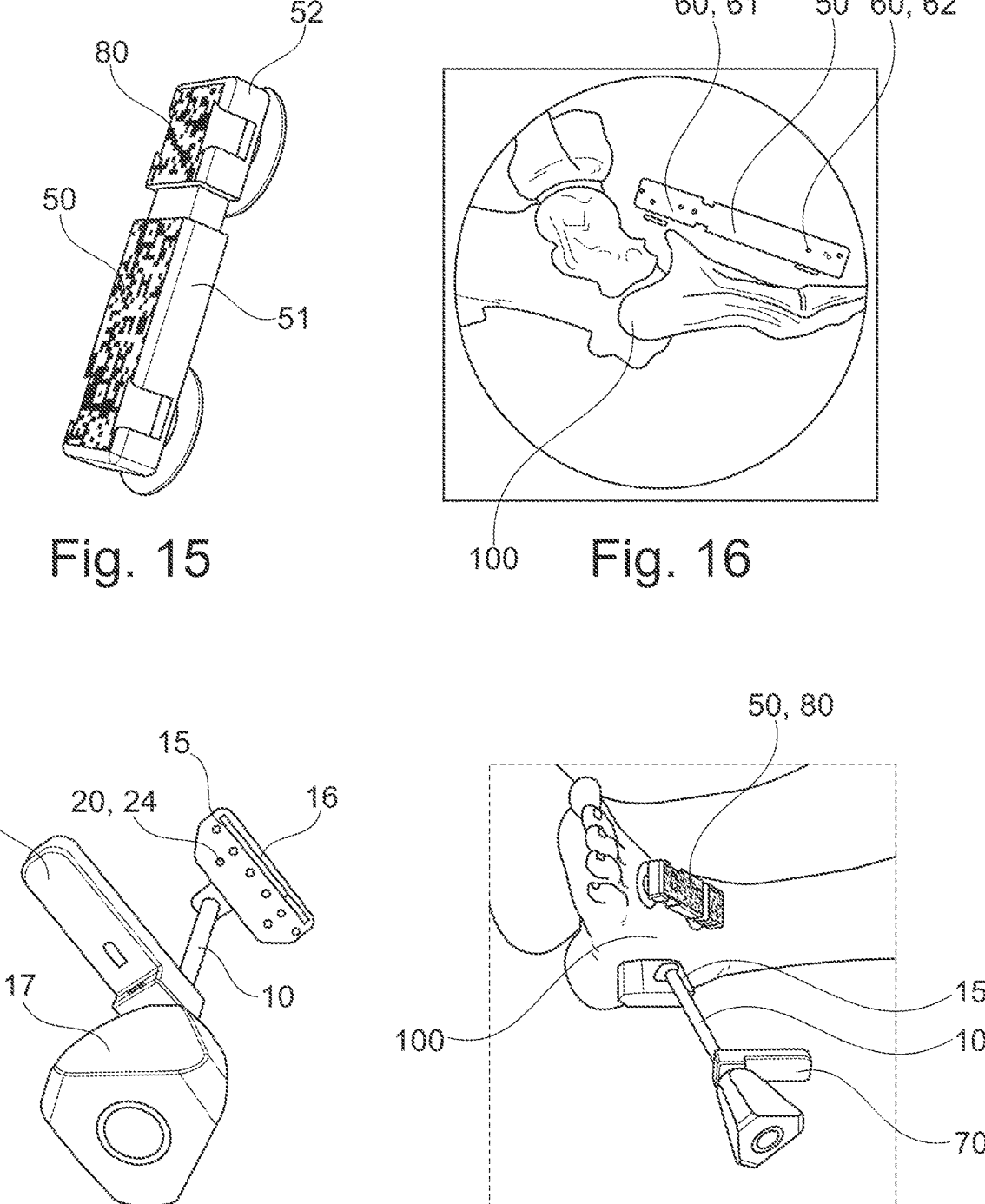
FIG. 15: illustrates a length adjustable reference body according to an exemplary embodiment.
FIG. 16: illustrates a radio image with reference body attached to the patient's anatomy according to an exemplary embodiment.
FIG. 17: illustrates a surgical guiding tool according to an exemplary embodiment having releasable mounted thereto a guiding body.
FIG. 18: illustrates the reference body of FIG. 16 adhered to patient's anatomy according to an exemplary embodiment.

FIG. 15 illustrates a length adjustable reference body 50, which may be a radiolucent body with a radio dense or radio-opaque geometry having a unique radio projection, as described above, which radio opaque geometry has a marking pattern which shows up in x-ray images. The reference body 50 may be composed of e.g. two parts, a first leg 51 and a second leg 52, which may be extractable with respect to each other. Both legs 51, 52 may have a separate radio dense sub pattern as described above, which is here not illustrated. The reference body 50 and/or each leg 51, 52 separately may have an optical pattern 80, as described above. It should be noted that the relative position of the both parts of the reference body as illustrated in FIG. 15 may be determined by connecting an optical imaging device to one of the parts of the surgical reference body, wherein the spatial determination works as it is described above for a surgical tool and a surgical reference device.

FIG. 16 illustrates a radio image or x-ray image with the reference body 50 attached to the patient's anatomy 100 and having a radio dense geometry 60, wherein each of the legs 51, 52 may have a separate radio dense sub geometry 61, 62.

FIG. 17 illustrates a surgical guiding tool 10 having e.g. releasable mounted thereto at a distal end a guiding body 15. The proximal end with the knob 17 has attached an optical imaging device 70, e.g. a camera, as described above. The guiding body 15 has a cutting guide trajectory 16, along which a cutting tool, not illustrated here, can be guided. The cutting guide trajectory can be formed by a slit in the body 15. The guiding body 16 has a radio dense geometry formed therein, here in form of a number of fiducial markers 24, which have a unique radio projection allowing determination of the orientation and position of the body 15 from the projection image of the fiducial markers.

FIG. 18 illustrated the reference body 50 of FIG. 16 adhered to the patient's anatomy 100. The reference body 50 has an optical patter attached thereto allowing determination of the position and orientation of the reference body 50 from an image taken by the optical imaging device 70. An optical pattern recognition allows determination of the relative position and orientation guiding body 15 with respect to the reference body 50. The radio dense geometry of the reference body 50 allows the determination of the relative position and orientation of the reference body 50 with respect to the patient's anatomy 10. Together, the optical identification and the radio identification allows determination of the relative position and orientation of the guiding body 15 and the patient's anatomy 100.

Figure 19:
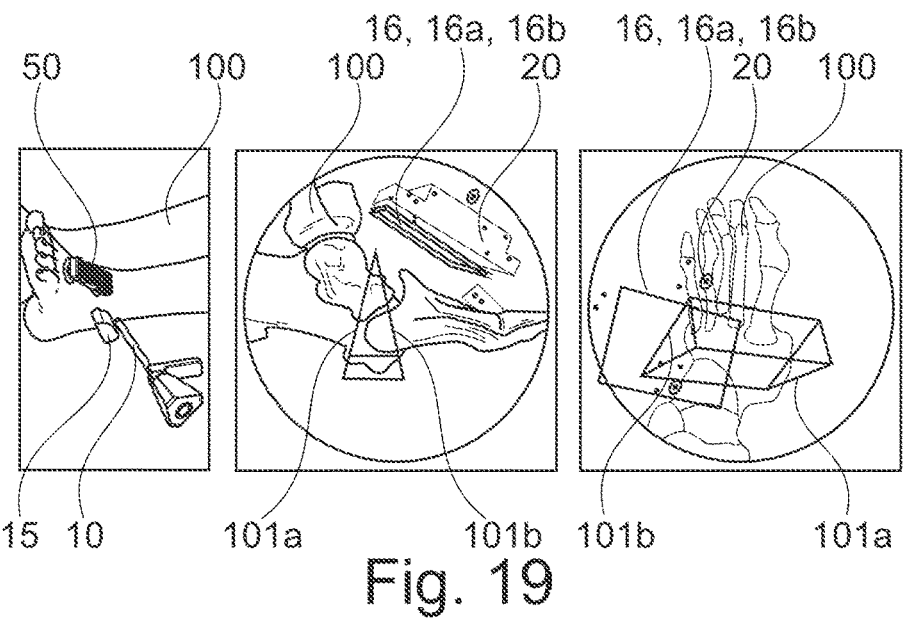
FIG. 19: illustrates the situation of FIG. 18, and a radio image thereof in a first viewing direction and in a second viewing direction.
Figure 21:
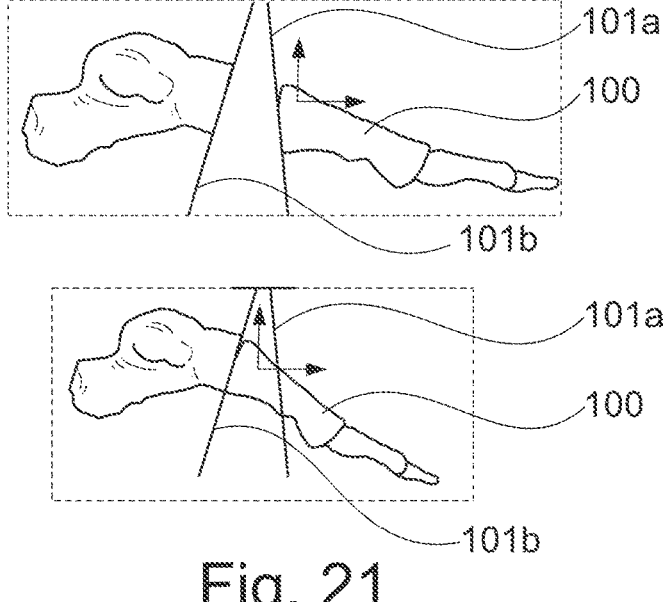
FIG. 21: illustrates a cut anatomy before and after re-composition.
Figure 23:
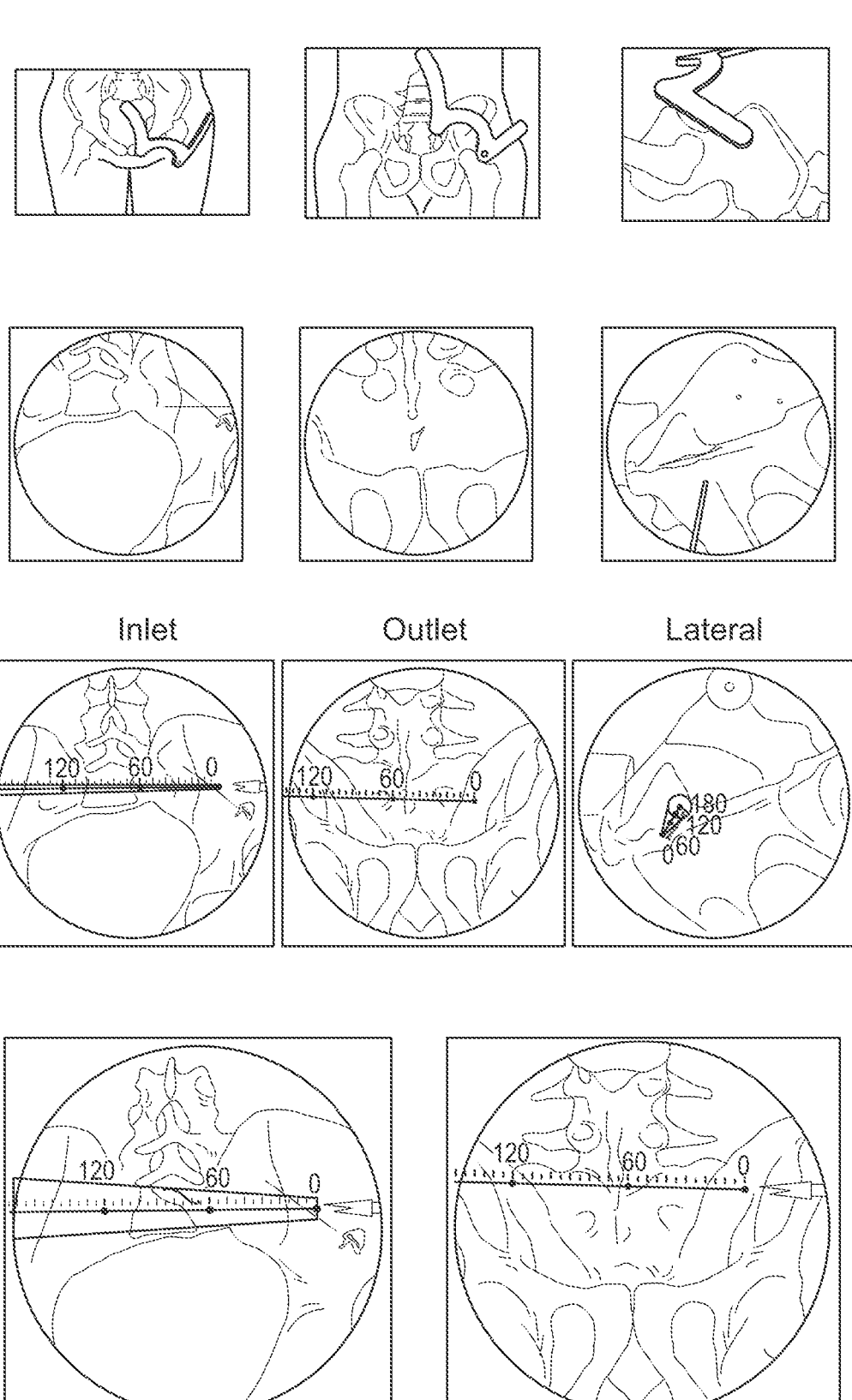
FIG. 23 illustrates different application samples of embodiments of the invention.

FIG. 19 illustrates on the left the situation illustrated in FIG. 18. FIG. 19 illustrated in the middle a radio image of the left illustrated situation from a first viewing direction. From the radio image, the patient's anatomy 100 and the reference body 50 with its radio dense geometry 20 can be achieved. An augmenting means may augment a cutting guide trajectory 16 corresponding to the radio dense geometry 20 of the body 15. If a first guiding body 15*a* and a second guiding body 15*b* are used, the augmenting means may augment a first cutting guide trajectory 16*a* and a second cutting guide trajectory 16*b* likewise. In addition thereto, a wedge can be augmented, which is defined by a first intended cutting plane 101*a* and a second intended cutting plane 101*b*, which intended cutting planes 101*a*, 101*b* may result from a planning procedure, where cuts for an osteotomy have to be carried out for repositioning of bone fragments, as illustrated in FIG. 21. FIG. 19 on the right side illustrated the same situation of the left illustration from a viewing direction of a radio image, which differs from the viewing direction of the middle illustration of FIG. 19. The guiding trajectory 16 is brought into alignment of the intended planes 101*a*, 101*b* by repositioning the surgical instrument 10 having mounted thereon the guiding body 15, where the unique projection 20 thereof is used for augmenting the guiding trajectory 16, 16*a*, 16*b*. There are two ways of aligning the guiding bodies 15 with the planned wedge, i.e. the intended planes 101*a*, 101*b*. One method is an incremental approach based on stereotactic imaging. Based on the position recognized by the system in the x-ray image it will augment additional alignment information based on this position. The illustration in FIG. 19 shows no proper alignment. The more the augmentation frame of the guiding trajectory 16 matches the planes 101*a*, 101*b* of the wedge, the better is the later cut. The other method is live tracking based on tracking via the optical imaging device 70, e.g. an optical camera. The difference to the stereotactic approach is the live feedback while moving the guiding body 15 without the need of taking repeated radio images.

Figure 20:
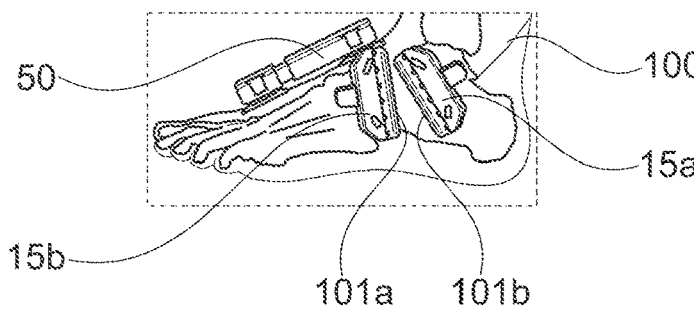
FIG. 20: illustrates schematic positioning of the reference body, a first guiding body and a second guiding body with respect to a patient's anatomy.

FIG. 20 illustrates the schematic positioning of the reference body 50, a first guiding body 15*a* and a second guiding body 15*b* with respect to a patient's anatomy. For the wedge osteotomy, two cutting guides or guiding bodies 15*a*, 15*b* are placed according the planning. The guiding body 15, 15*a*, 15*b* itself can be detached from the surgical instrument or handle and fixated by k-wires to the bone. After the two cuts, the anatomical structures can be repositioned, as illustrated in FIG. 21, top: cut, bottom repositioned. With the reference-body 50 still in the radio image, it can also be verified to the planned outcome, as illustrated in FIG. 21 bottom. FIG. 21 illustrates in the upper illustration a planning part of a wedge based on 3D CT data. The wedge is formed by a first intended cutting plane 101*a* on the patient's anatomy 100 and a second intended cutting plane 100*b* at the patient's anatomy 100. The 3D data set is than matched manually or automatically to the intraoperative acquired radio images of a patient's anatomy so that the planned wedge can be transferred to those images, as illustrated in FIG. 19 middle and right with the illustrated wedge therein.

Figure 22:
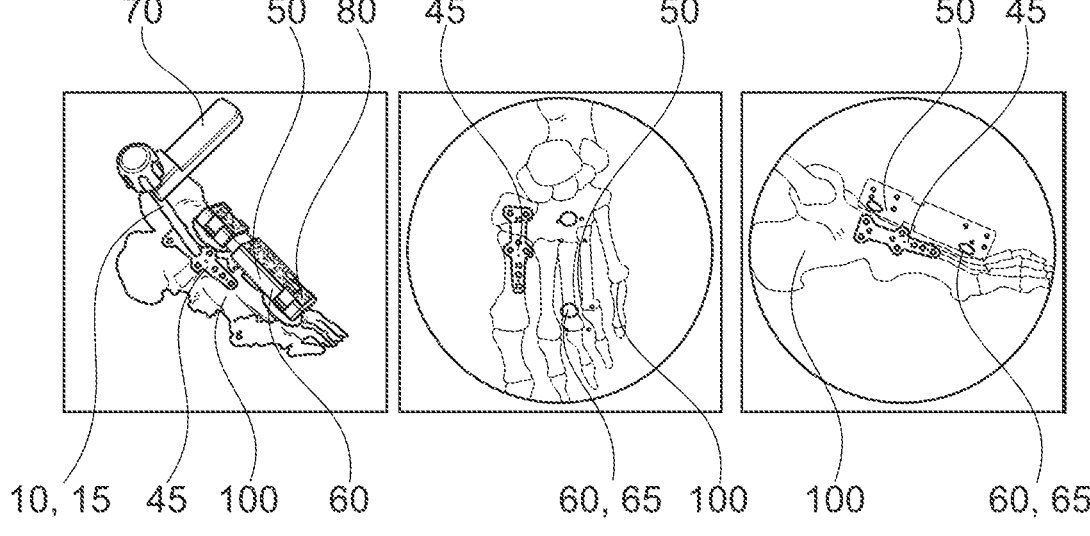
FIG. 22: illustrates a surgical instrument in form of an inserter with optical camera attached to an implant according to an exemplary embodiment.

FIG. 22 illustrates a surgical instrument 10 in form of an inserter with optical camera 70 attached to an implant 45 in form of a plate or nail, This inserter can be used for minimal invasive placement so that the system provides live feedback on the previously taken radio image where the position and orientation of the implant is determined relative to the anatomy 100. A similar approach can be used for screw planning and placement, either by using the camera 70, or based on a stereotactic approach. Markers or a radio dense geometry 60, 65 can be added or the camera 70 can be attached to e.g. a drill guide 10, 15 and providing information about length and trajectory.

REFERENCES

1 surgical guiding system for computer-assisted-surgery CAS
2 surgical tracking system
10 surgical guiding device/surgical instrument
11 proximal end of the surgical guiding device/surgical instrument
12 distal end of the surgical guiding device/surgical instrument
15 guiding body
15*a* hollow shaft guiding body
15*b* guiding channel of guiding body
16 guiding trajectory/cutting plane trajectory of the guiding body/operating trajectory of surgical instrument
16*a* first cutting plane trajectory of the guiding body of surgical instrument
16*b* second cutting plane trajectory of the guiding body of surgical instrument
17 knob/handle of surgical guiding device
17*a* mechanical interface of surgical instrument for optical imaging device or pattern
18 tip of surgical guiding device
18*a* blade/tool at the tip of surgical guiding device
19 virtual visualization of a guiding body/an orientation of the guiding body
20 radio dense geometry of surgical guiding device
21 first radio dense sub-geometry of surgical guiding device
22 second radio dense sub-geometry of surgical guiding device
23 third radio dense sub-geometry of surgical guiding device
24 fiducial markers
25 radio projection of radio dense geometry of surgical guiding device
26 radio projection of the first sub-geometry of surgical guiding device
27 radio projection of the second sub-geometry of surgical guiding device
28 unique radio projection of the third sub-geometry of surgical guiding device
29 complementary pattern of radio projections of first/second sub-geometry
30 image processing device
32 recognition means for pattern recognition
36 visualization means
38 augmenting means for augmenting the guiding trajectory
39 reproducible scale along augmented guiding trajectory
45 surgical implant/surgical tool
46 traveling path of a surgical implant/surgical tool to be inserted and guided/extended operating trajectory of surgical instrument
50 surgical reference body
51 first leg of surgical reference body
51*a* first end of first leg
51*b* second end of first leg
51*c* center line of first leg
52 second leg of surgical reference body
52*a* first end of second leg
52*b* second end of second leg

52*c* center line of second leg
53 joining portion of first and second leg of surgical reference body
53*c* joining point of central lines of first/second leg
54 first sub-leg of surgical reference body
54*a* first end of first sub-leg
54*b* second end of first sub-leg
54*c* center line of first sub-leg
55 second sub-leg of surgical reference body
55*a* first end of second sub-leg
55*b* second end of second sub-leg
55*c* center line of second sub-leg
56 joining portion of first and second sub-leg of surgical reference body
56*c* joining point of central lines of first/second sub-leg
57 fixing hole/apex-pin hole in surgical reference body
57*a* mechanical interface of surgical reference body for optical imaging device or pattern
58 adhering means of surgical reference body/surgical guiding body
59 anatomically adapted surface of first/second (sub-)leg
60 radio dense geometry of surgical reference body
61 first radio dense sub-geometry of surgical reference body
62 second radio dense sub-geometry of surgical reference body
63 third radio dense sub-geometry of surgical reference body
64 fiducial markers
65 unique radio projection of radio dense geometry of surgical reference body
66 unique radio projection of the first sub-geometry of surgical reference body
67 unique radio projection of the second sub-geometry of surgical reference body
68 unique radio projection of the third sub-geometry of surgical reference body
70 optical imaging device
71 viewing direction of optical imaging device
77*a* mechanical interface of optical imaging device for instrument or reference body
80 optical pattern
80*a* optical sub-pattern
82 even raster of optical pattern
83 honeycomb raster of optical pattern
87*a* mechanical interface of optical imaging device for instrument or reference body
100 patient's anatomy
101 intended cutting plane at patient's anatomy
101*a* first intended cutting plane at patient's anatomy
101*b* second intended cutting plane at patient's anatomy
S30 processing imaging
S32 recognizing pattern(s)
S33 comparing recognized (sub-)pattern(s) with predetermined pattern(s)
S34 determining position and orientation of (sub-)pattern(s)
S36 visualization
S38 augmenting for augmenting the guiding trajectory
S70 taking optical imaging
The invention claimed is:

1. A surgical tracking system for tracking a surgical instrument with respect to a surgical reference body, the surgical tracking system comprising:
an optical imaging device representing a position and orientation of the surgical instrument, the optical imaging device having a predetermined viewing direction,

24 an optical pattern representing a position and orientation of the surgical reference body, the optical pattern having at least one unique optical sub-pattern, which allows determination of a relative position and orientation of said surgical reference body with respect to the position and orientation of said surgical instrument,
an image processing device (30) configured to:
recognize the position and orientation of the at least one sub-pattern of the optical pattern with respect to a position and viewing direction of the imaging device based on an image taken from the optical imaging device and a stored representation of the optical pattern, and
virtually visualize the surgical instrument represented by the optical imaging device and virtually visualize a surgical reference body represented by the optical pattern,
wherein the surgical reference body includes:
a radio dense geometry having a first radio dense sub-geometry and a second radio dense sub-geometry each being fixedly and spatially reproducibly connected to the surgical reference body,
a first reference body portion having an anatomically adapted surface for a patient's anatomy,
a second reference body portion having an anatomically adapted surface for a patient's anatomy,
wherein each of the first radio dense sub-geometry and the second radio dense sub-geometry has a unique radio projection for each proximal to distal orientation of the surgical reference body, so that each of the first radio dense sub-geometry and the second radio dense sub-geometry alone allows determination of the spatial position and orientation of the surgical reference body based on a two dimensional radio projection of at least a part of the surgical reference body,
wherein the first radio dense sub-geometry is allocated to the first reference body portion, and the second radio dense sub-geometry is allocated to the second reference body portion.

2. The surgical tracking system of claim 1, wherein the image processing device is further configured to:
augment a predetermined operating trajectory of the surgical instrument onto the virtual visualization of the surgical instrument, based on a recognized position and orientation of the at least one sub-pattern of the optical pattern with respect to the position and predetermined viewing direction of the imaging device, so as to visualize an operating path of the surgical instrument relative to a surgical reference body represented by the optical pattern.

3. The surgical tracking system of claim 1, wherein the optical imaging device comprises a mechanical interface configured to be coupled to a positive fit receptacle of one of the surgical instrument and the surgical reference body for forming a unit having a reproducible relation between a geometry of said one of the surgical instrument and the surgical reference body, and the position and predetermined viewing direction of the optical imaging device, wherein the surgical instrument includes a mechanical interface for the mechanical interface of the optical imaging device so as to form a reproducible relation between the geometry of the surgical instrument and the position and predetermined viewing direction of the optical imaging device.

4. The surgical tracking system of claim 3,
wherein the radio dense geometry has a unique radio projection for each proximal to distal orientation of the surgical reference body, so that the radio dense geometry allows determination of the spatial position and orientation of the surgical reference body based on a two dimensional radio projection of at least a part of the surgical reference body.

5. The surgical tracking system of claim 3, wherein the radio dense geometry has the first radio dense sub-geometry, the second radio dense sub-geometry, and a third radio dense sub-geometry each being fixedly and spatially reproducibly connected to the surgical reference body,
a first leg having an anatomically adapted surface for a patient's anatomy,
a second leg having an anatomically adapted surface for a patient's anatomy,
wherein the first leg with a first end is connected to a first end of the second leg at a leg joining portion,
wherein each of the first radio dense sub-geometry, the second radio dense sub-geometry, and the third radio dense sub-geometry has a unique radio projection for each proximal to distal orientation of the surgical reference body, so that each of the first radio dense sub-geometry, the second radio dense sub-geometry, and the third radio dense sub-geometry alone allows determination of the spatial position and orientation of the surgical reference body based on a two dimensional radio projection of at least a part of the surgical reference body, and
wherein the first radio dense sub-geometry is allocated to a second end of the first leg, the second radio dense sub-geometry is allocated to a second end of the second leg, and the third radio dense sub-geometry is allocated to the leg joining portion of the first leg and the second leg.

6. The surgical tracking system of claim 3,
wherein the surgical instrument is a surgical cutting guide device including:
a guiding body having a planar cutting extension from a proximal end of the surgical cutting guide device to a distal end of the surgical cutting guide device, and being adapted for guiding a surgical cutting tool, and having a cutting plane trajectory extending along the guiding body and succeeding in distal direction along a traveling path of a surgical cutting tool to be inserted and guided,
the radio dense geometry being located in a predetermined spatial position and orientation with respect to the guiding body, and being adapted for providing a unique radio projection for each proximal to distal orientation of the guiding body,
wherein the surgical reference body includes:
the radio dense geometry being fixedly and spatially reproducibly connected to the surgical reference body,
wherein the radio dense geometry has a unique radio projection for each proximal to distal orientation of the surgical reference body, so that the radio dense geometry allows determination of the spatial position and orientation of the surgical reference body based on a two dimensional radio projection of at least a part of the surgical reference body.

7. The surgical tracking system of claim 1, wherein the optical imaging device comprises a mechanical interface configured to be coupled to a positive fit receptacle of the surgical instrument for forming a unit having a reproducible relation between a geometry of the surgical instrument, and the position and predetermined viewing direction of the optical imaging device, wherein the surgical reference body includes a mechanical interface for the mechanical interface of the optical imaging device so as to form a reproducible relation between the geometry of the surgical reference body and the position and predetermined viewing direction of the optical imaging device.

8. The surgical tracking system of claim 1, wherein the optical pattern comprises a mechanical interface configured to be coupled to a positive fit mechanical interface of the surgical instrument for forming a unit having a reproducible relation between a geometry of the surgical instrument, and the position and orientation of the optical pattern (80), wherein the surgical instrument includes the mechanical interface for the mechanical interface of the optical pattern so as to form a reproducible relation between the geometry of the surgical instrument and the position and orientation of the optical pattern.

9. The surgical tracking system of claim 1, wherein the optical pattern comprises a mechanical interface configured to be coupled to a positive fit mechanical interface of one of the surgical instrument and the surgical reference body for forming a unit having a reproducible relation between a geometry of said one of the surgical instrument and the surgical reference body, and the position and orientation of the optical pattern, wherein the surgical reference body includes the mechanical interface for the mechanical interface of the optical pattern so as to form a reproducible relation between the geometry of the surgical reference body and the position and orientation of the optical pattern.

10. The surgical tracking system of claim 1, wherein the optical imaging device is inseparably connected to the surgical instrument so as to form a reproducible relation between the geometry of the surgical instrument and the position and orientation of the optical imaging device, and wherein the optical pattern is inseparably connected to the surgical reference body so as to form a reproducible relation between the geometry of the surgical reference body and the position and orientation of the optical pattern.

11. The surgical tracking system of claim 1, wherein the optical pattern is inseparably connected to the surgical instrument so as to form a reproducible relation between the geometry of the surgical instrument and the position and orientation of the optical pattern.

12. The surgical tracking system of claim 1, wherein the optical pattern is composed of at least one of:
a geometrically even raster of light and dark fields, which includes a raster of squared light and dark fields, which includes a raster of light and black fields, and/or a geometrically even raster of fields of different colors, which includes a raster of squared colored fields, which includes a raster of color gradient fields.

13. The surgical tracking system of claim 1, wherein the optical pattern is composed of a honeycomb raster of light and dark fields, which includes a raster of light and dark circles or hexagons in a honeycomb raster, which includes a raster of light and black circles or hexagons.

14. The surgical tracking system of claim 13,
wherein the guiding body is a first guiding body releasably mountable to the surgical cutting guide device and including adhering means for adhering the first guiding body to a patient's anatomy so that a first cutting plane trajectory extending along the first guiding body and succeeding in a distal direction along a traveling path of a surgical cutting tool to be inserted and guided aligns with a first intended cutting plane at the patient's anatomy,
the surgical cutting guide device further including a second first guiding body releasably mountable to the surgical cutting guide device and including adhering means for adhering the second guiding body to a patient's anatomy so that a second cutting plane trajectory extending along the second guiding body and succeeding in a distal direction along a traveling path of a surgical cutting tool to be inserted and guided aligns with a second intended cutting plane at the patient's anatomy, wherein the second cutting plane trajectory is inclined with respect to the first cutting plane trajectory, the surgical tracking system configured to augment at least one of the first cutting plane trajectory and the second cutting plane trajectory with respect to at least one of the first intended cutting plane and the second intended cutting plane at the patient's anatomy, based on at least one of the optical pattern and the radio dense geometry having a unique radio projection, provided on each of the surgical reference body, the first guiding body and the second guiding body, and wherein the surgical tracking system is adapted for instructing a surgeon on how to align at least one of the first cutting plane trajectory and the second cutting plane trajectory with respect to at least one of the first intended cutting plane and the second intended cutting plane.

15. The surgical tracking system of claim 1, wherein the optical pattern is composed of a honeycomb raster of fields of different colors, which includes a raster of colored circles or hexagons in a honeycomb raster, which includes a raster of color gradient circles or hexagons.

16. A method for visualizing tracking of a surgical instrument with respect to a surgical reference body, the method comprising:

taking an optical image toward a predetermined viewing direction by an imaging device mounted with the predetermined viewing direction onto the surgical instrument, of an optical pattern mounted with a predetermined relative position and orientation to the surgical reference body, wherein the optical pattern has at least one unique optical sub-pattern, which allows determination of a relative position and orientation of said surgical reference body with respect to the position and orientation of said surgical instrument, processing a taken optical image of the optical pattern by recognizing the at least one sub-pattern of the optical pattern, comparing the recognized optical sub-pattern with a stored representation of the optical pattern, and determining from a size, an orientation and a distortion of the recognized sub-pattern compared to the stored representation of the optical pattern the position and orientation of the surgical instrument with respect to the orientation and position of the surgical reference body, wherein the surgical reference body includes:

a radio dense geometry having a first radio dense sub-geometry and a second radio dense sub-geometry each being fixedly and spatially reproducibly connected to the surgical reference body, a first reference body portion having an anatomically adapted surface for a patient's anatomy, a second reference body portion having an anatomically adapted surface for a patient's anatomy, wherein each of the first radio dense sub-geometry and the second radio dense sub-geometry has a unique radio projection for each proximal to distal orientation of the surgical reference body, so that each of the first radio dense sub-geometry and the second radio dense sub-geometry alone allows determination of the spatial position and orientation of the surgical reference body based on a two dimensional radio projection of at least a part of the surgical reference body, wherein the first radio dense sub-geometry is allocated to the first reference body portion, and the second radio dense sub-geometry is allocated to the second reference body portion.

17. The method of claim 16, further comprising:

visualizing the surgical instrument represented by the optical imaging device and visualizing the surgical reference body represented by the optical pattern.

18. The method of claim 17, further comprising:

augmenting a predetermined operating trajectory of the surgical instrument onto a virtual visualization of the surgical instrument, based on a recognized position and orientation of the at least one sub-pattern of the optical pattern with respect to a position and viewing direction of the imaging device, so as to visualize an operating path of the surgical instrument relative to the surgical reference body represented by the optical pattern.

19. A surgical tracking system for tracking a surgical instrument with respect to a surgical reference body, the surgical tracking system comprising:

an optical imaging device representing a position and orientation the surgical instrument, the optical imaging device having a predetermined viewing direction;

an optical pattern representing a position and orientation of the surgical reference body, the optical pattern having at least one unique optical sub-pattern, which allows determination of a relative position and orientation of said surgical instrument with respect to the position and orientation of said surgical reference body;

an image processing device configured to recognize the position and orientation of the at least one sub-pattern of the optical pattern with respect to a position and viewing direction of the imaging device based on an image taken from the optical imaging device and a stored representation of the optical pattern, and configured to determine the relative position and orientation of said surgical instrument with respect to the position and orientation of said surgical reference body, wherein the surgical reference body includes:

a radio dense geometry having a first radio dense sub-geometry and a second radio dense sub-geometry each being fixedly and spatially reproducibly connected to the surgical reference body, a first reference body portion having an anatomically adapted surface for a patient's anatomy, a second reference body portion having an anatomically adapted surface for a patient's anatomy, wherein each of the first radio dense sub-geometry and the second radio dense sub-geometry has a unique radio projection for each proximal to distal orientation of the surgical reference body, so that each of the first radio dense sub-geometry and the second radio dense sub-geometry alone allows determination of the spatial position and orientation of the surgical reference body based on a two dimensional radio projection of at least a part of the surgical reference body, wherein the first radio dense sub-geometry is allocated to the first reference body portion, and the second radio dense sub-geometry is allocated to the second reference body portion.

\* \* \* \* \*